(12) United States Patent
Parvulescu et al.

(10) Patent No.: US 9,446,390 B2
(45) Date of Patent: Sep. 20, 2016

(54) PROCESS FOR PREPARING ACRYLIC ACID USING AN ALUMINUM-FREE ZEOLITIC MATERIAL

(71) Applicant: BASF SE, Ludwigshafen (DE)

(72) Inventors: Andrei-Nicolae Parvulescu, Ruppertsberg (DE); Armin Lange De Oliveira, Heidelberg (DE); Michael Lejkowski, Neckargemuend (DE); Nicolai Tonio Woerz, Darmstadt (DE); Marco Hartmann, Woerth (DE); Kazuhiko Amakawa, Mannheim (DE); Michael Goebel, Mannheim (DE); Ulrich Mueller, Neustadt (DE); Mathias Feyen, Laudenbach (DE); Yong Liu, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/724,204

(22) Filed: May 28, 2015

(65) Prior Publication Data

US 2015/0343431 A1 Dec. 3, 2015

Related U.S. Application Data

(60) Provisional application No. 62/004,961, filed on May 30, 2014.

(30) Foreign Application Priority Data

May 30, 2014 (DE) .................. 10 2014 008 080

(51) Int. Cl.
| | | |
|---|---|---|
| *B01J 29/70* | (2006.01) | |
| *B01J 29/40* | (2006.01) | |
| *C07C 51/353* | (2006.01) | |

(52) U.S. Cl.
CPC ........... *B01J 29/7088* (2013.01); *B01J 29/405* (2013.01); *B01J 29/7007* (2013.01); *B01J 29/7038* (2013.01); *B01J 29/7057* (2013.01); *C07C 51/353* (2013.01)

(58) Field of Classification Search
CPC B01J 29/7088; B01J 29/7057; B01J 29/405; B01J 29/7007; B01J 29/7038; C07C 51/353; C07C 57/04
See application file for complete search history.

(56) References Cited

U.S. PATENT DOCUMENTS

| | | | |
|---|---|---|---|
| 6,242,406 B1 * | 6/2001 | Katsuda ................. | C11D 1/146 510/357 |
| 2012/0071687 A1 | 3/2012 | Herzog et al. | |
| 2012/0071688 A1 | 3/2012 | Herzog et al. | |
| 2013/0085294 A1 | 4/2013 | Peterson et al. | |
| 2014/0364644 A1 * | 12/2014 | Nagaki ................. | C07C 51/353 560/211 |

FOREIGN PATENT DOCUMENTS

| | | |
|---|---|---|
| DE | 10 2010 040 921 A1 | 3/2012 |
| DE | 10 2010 040 923 A1 | 3/2012 |
| WO | WO 2013/117537 A1 | 8/2013 |

OTHER PUBLICATIONS

James F. Vitcha, et al., "Vapor Phase Aldol Reaction—Acrylic Acid by the Reaction of Acetic Acid and Formaldehyde" I & EC Product Research and Development, vol. 5, No. 1, Mar. 1966, pp. 50-53.
Piotr T. Wierzchowski, et al., "Aldol Condensation in Gaseous Phase by Zeolite Catalysts" Catalysis Letters 9, 1991, pp. 411-414.

* cited by examiner

*Primary Examiner* — Shailendra Kumar
(74) *Attorney, Agent, or Firm* — Oblon, McClelland, Maier & Neustadt, L.L.P.

(57) ABSTRACT

The present invention relates to a process for preparing acrylic acid comprising (i) providing a stream comprising a formaldehyde source and acetic acid and (ii) contacting this stream with an aldol condensation catalyst comprising a zeolitic material, wherein the framework structure of the zeolitic material in (ii) includes Si and O, and has a molar Al:Si ratio of 0:1 to 0.001:1, and wherein the framework structure of the zeolitic material in (ii), in addition to Si and any Al, comprises one or more elements selected from the group consisting of tetravalent elements Y other than Si and trivalent elements X other than Al.

18 Claims, 9 Drawing Sheets

Fig. 4 (FD0032-01 Sn-ZSM-5)

PROCESS FOR PREPARING ACRYLIC ACID USING AN ALUMINUM-FREE ZEOLITIC MATERIAL

This application claims benefit of 62/004,961, filed on May 30, 2014.

The present invention relates to a process for preparing acrylic acid by contacting a stream comprising a formaldehyde source and acetic acid with an aldol condensation catalyst comprising an aluminum-free zeolitic material.

Acrylic acid, an important monomer for production of homo- and copolymers, is typically obtained by a heterogeneously catalyzed two-stage partial oxidation proceeding from propene, with acrolein as intermediate.

Vitcha and Sims, I & EC Product Research and Development, Vol. 5, No. 1, March 1966, pages 50 to 53, describe the synthesis of acrylic acid in a gas phase reaction proceeding from acetic acid and formaldehyde. Catalysts described are firstly aluminosilicates wherein the negative framework charges are preferably compensated for by alkali metal and alkaline earth metal cations. A second type of catalyst described is hydroxide from the group consisting of alkali metal hydroxides, alkaline earth metal hydroxides and aluminum hydroxide (preferably KOH, NaOH, $Ca(OH)_2$ and $Mg(OH)_2$), applied to inert supports (e.g. amorphous silicon dioxide).

Wierzchowsky and Zatorski, Catalysis Letters 9 (1991), pages 411 to 414, describe the aldol condensation of formaldehyde prepared in situ with methyl propionate in the gas phase over various zeolitic catalysts.

DE 2010 040 921 A1 describes a process for preparing acrylic acid from methanol and acetic acid, wherein methanol is first converted to formaldehyde and the latter is reacted with acetic acid to give acrylic acid. Preference is given to using catalysts wherein the active composition is a vanadium-phosphorus oxide and/or a vanadium-phosphorus oxide doped with elements other than vanadium and phosphorus.

DE 2010 040 923 A1 describes a process for preparing acrylic acid from ethanol and formaldehyde, wherein ethanol is first converted to acetic acid and the latter is reacted with formaldehyde to give acrylic acid. Here, preference is likewise given to using catalysts wherein the active composition is a vanadium-phosphorus oxide and/or a vanadium-phosphorus oxide doped with elements other than vanadium and phosphorus.

US 2013/0085294 A1 describes a process for preparing acrylic acid from acetic acid and an alkylating agent such as formaldehyde. The catalysts used comprise titanium and vanadium, and optionally oxidic additives such as $SiO_2$, $Al_2O_3$ and $ZrO_2$. For the merely optional supporting of this catalytically active component, zeolitic materials are among those mentioned as supports.

In spite of the numerous processes developed for preparation of acrylic acid, there was still a need to develop an improved process for preparing acrylic acid proceeding from a formaldehyde source and acetic acid. One of the problems addressed by the present invention was therefore that of providing an improved process for preparing acrylic acid proceeding from a formaldehyde source and acetic acid.

It has been found that, surprisingly, such an improved process can be provided when the aldol condensation catalyst used is a catalyst comprising a specific zeolitic material as catalytically active component. More particularly, it has been found that the improved process stands out in a positive way from the known processes in terms of at least one of the parameters of carbon conversion, yield of acrylic acid, selectivity of acrylic acid formation and space-time yield, and the process improved in accordance with the invention especially also stands out in a positive way from the known processes in terms of all these parameters.

The present invention therefore relates to a process for preparing acrylic acid, comprising
(i) providing a stream S4 comprising a formaldehyde source and acetic acid;
(ii) contacting the stream S4 with an aldol condensation catalyst comprising a zeolitic material to obtain a stream S6 comprising acrylic acid;
wherein the framework structure of the zeolitic material in (ii) includes Si and O, and has a molar Al:Si ratio in the range from 0:1 to 0.001:1;
and wherein the framework structure of the zeolitic material in (ii), in addition to Si and any Al, comprises one or more elements selected from the group consisting of tetravalent elements Y other than Si and trivalent elements X other than Al.

The term "aldol condensation" as used in the context of the present invention is understood to mean a condensation reaction in which an alpha,beta-unsaturated carbonyl compound, acrylic acid in the present case, is formed from two suitable carbonyl compounds, acetic acid and formaldehyde in the present case, with elimination of water.

Step (i)

In step (i) of the process according to the invention, a stream S4 comprising a formaldehyde source and acetic acid is provided.

A useful formaldehyde source for the process according to the invention is in principle any suitable formaldehyde source which affords formaldehyde under the conditions of the contacting in (ii) or in the provision in (i). The formaldehyde source is preferably anhydrous. According to the present invention, the formaldehyde source is preferably selected from the group consisting of formaldehyde, trioxane, paraformaldehyde and a mixture of two or more thereof. In a particularly preferred embodiment of the present invention, trioxane is used as formaldehyde source, and trioxane is further preferably used as the sole formaldehyde source in the process. Trioxane is a heterocyclic compound from the group of the acetals, which forms through trimerization of formaldehyde and depolymerizes again on heating to 150 to 200° C. to give monomeric formaldehyde. Paraformaldehyde is the short-chain polymer of formaldehyde, typically having a degree of polymerization of 8 to 100.

A useful source for the acetic acid is in principle any suitable source comprising at least a proportion of acetic acid, preference being given to preferably acetic acid having a purity of at least 95% by weight, further preferably at least 96% by weight, further preferably at least 97% by weight, further preferably at least 98% by weight, further preferably at least 99% by weight. Particular preference is given to the acetic acid in pure form as glacial acetic acid.

Stream S4 may in principle have any molar ratio of acetic acid to formaldehyde suitable for obtaining acrylic acid in the process according to the invention, formaldehyde being obtained and/or obtainable from the formaldehyde source. Preferably, the molar ratio of acetic acid to formaldehyde, obtained and/or obtainable from the formaldehyde source, in stream S4 is in the range from 0.01:1 to 10:1. Further preferably, the molar ratio of acetic acid to formaldehyde, obtained and/or obtainable from the formaldehyde source, in stream S4 is in the range from 0.1:1 to 9:1, further preferably from 0.5:1 to 8.5:1. Further preferably, the molar ratio of acetic acid to formaldehyde, obtained and/or obtainable from the formaldehyde source, in stream S4 is in the range from 1:1 to 8:1, further preferably from 1.5:1 to 5:1, further preferably from 1.7:1 to 4.7:1, further preferably from 2:1 to 4.4:1, further preferably from 2.5:1 to 4.1:1.

In principle, stream S4 can be provided at any temperature suitable for the process according to the invention. Stream S4 can therefore be provided, for example, at a temperature corresponding to room temperature, or else be heated prior to contacting with an aldol condensation catalyst comprising a zeolitic material to obtain a stream S6 comprising acrylic acid. If stream S4 is heated, the heat sources in the context of the process according to the invention are unrestricted, and so any heat source is useful in principle. Thus, it is also possible that stream S4 is heated with the aid of a product stream of the present process. For example, stream S4 can be heated to a temperature of 190° C. or 200° C. It is equally conceivable that stream S4 is cooled to a temperature suitable for the process according to the invention, if individual components or else all the components of stream S4 would otherwise have an undesirably high temperature for the process according to the invention. For the process according to the invention, it is preferable that stream S4 is brought to a temperature of 150 to 250° C. before being contacted with an aldol condensation catalyst comprising a zeolitic material to obtain a stream S6. It is further preferable that stream S4 is brought to a temperature of 180 to 220° C. before being contacted with an aldol condensation catalyst comprising a zeolitic material to obtain a stream S6.

As well as acetic acid and a formaldehyde source, the stream S4 provided in (i) may comprise further components. For example, diluents are an option here. It is possible here to use all suitable diluents which are known to those skilled in the art and allow performance of the process according to the invention to obtain acrylic acid. The diluents are preferably selected from the group consisting of nitrogen, carbon monoxide, carbon dioxide, ethene, acetone, water and a combination of two or more thereof. Further preferably, the diluent comprises nitrogen. Consequently, the present invention also relates to a process wherein stream S4 further comprises one or more diluents, preferably selected from the group consisting of nitrogen, carbon monoxide, carbon dioxide, ethene, acetone, water and a combination of two or more thereof, preferably nitrogen. The diluent can, for example, be supplied to the process from the outside. It is equally possible to recycle the diluent within the process by means of one or more recycling steps. It is equally possible to supply a portion of the diluent to the process from the outside, and to recycle a further portion of the diluent within the process by means of one or more recycling steps.

With regard to the ratio between acetic acid and formaldehyde source relative to one or more diluents, stream S4 may in principle have any desired suitable ratio. If nitrogen is the diluent, the proportion in stream S4 is preferably in the range from 0.1% to 80% by volume, further preferably from 0.1% to 70% by volume, further preferably from 0.1% to 60% by volume, further preferably from 0.1% to 50% by volume, further preferably from 0.1% to 20% by volume, further preferably from 0.1% to 10% by volume, further preferably from 0.1% to 5% by volume. If carbon dioxide is the diluent, the proportion in stream S4 is preferably in the range from 0.1% to 50% by volume, further preferably from 0.1% to 20% by volume, further preferably from 0.1% to 10% by volume, further preferably from 0.1% to 5% by volume. If ethene is the diluent, the proportion in stream S4 is preferably in the range from 0.1% to 50% by volume, further preferably from 0.1% to 20% by volume, further preferably from 0.1% to 10% by volume, further preferably from 0.1% to 5% by volume. If acetone is the diluent, the proportion in stream S4 is preferably in the range from 0.1% to 50% by volume, further preferably from 0.1% to 20% by volume, further preferably from 0.1% to 10% by volume, further preferably from 0.1% to 5% by volume. If water is the diluent, the proportion in stream S4 is preferably in the range from 0.1% to 40% by volume, further preferably from 0.1% to 35% by volume, further preferably from 0.1% to 30% by volume.

Step (ii)

The Zeolitic Material

The framework structure of the zeolitic material in (ii) includes Si and O. In addition, the framework structure of the zeolitic material in (ii) of the process according to the invention has a molar Al:Si ratio in the range from 0:1 to 0.001:1. It is preferable that the framework structure of the zeolitic material in (ii) has a molar Al:Si ratio of aluminum to silicon in the range from 0:1 to 0.0001:1, preferably from 0:1 to 0.00001:1, further preferably from 0:1 to 0.000001:1. Preferably, the framework structure of the zeolitic material in (ii) is free of aluminum. "Free of aluminum" in this context of the present invention means that aluminum is present in the zeolitic material only in traces, i.e. in the form of an impurity at most, if at all.

According to the present invention, it is further preferable that the aldol condensation catalyst used in the process according to the invention likewise comprises only little or no aluminum. It is further preferable that the aldol condensation catalyst in (ii) has a molar Al:Si ratio of aluminum to silicon in the range from 0:1 to 0.001:1, preferably from 0:1 to 0.0001:1, further preferably from 0:1 to 0.00001:1. More preferably, the aldol condensation catalyst in (ii) is free of aluminum. "Free of aluminum" in this context of the present invention means that aluminum is present in the aldol condensation catalyst only in traces, i.e. in the form of an impurity at most, if at all.

The framework structure of the zeolitic material in (ii) of the process according to the invention, in addition to Si, O and any Al, comprises one or more elements selected from the group consisting of tetravalent elements Y other than Si and trivalent elements X other than Al.

In principle, any tetravalent element other than Si is useful for the tetravalent element Y present in the framework structure. Preferably, Y is selected from the group consisting of Sn, Ti, Zr, Ge, V and a combination of two or more thereof, further preferably from the group consisting of Sn, Ti, Ge and a combination of two or more thereof, further preferably from the group consisting of Sn, Ti and a combination thereof.

Further preferably, the framework structure of the zeolitic material in (ii) comprises $YO_2$ where Y is selected from the group consisting of Sn, Ti, Ge and a combination thereof. Further preferably, the framework structure of the zeolitic material in (ii) comprises $YO_2$ where Y is selected from the group consisting of Sn, Ti and a combination thereof. According to the present invention, further preference is given to zeolitic materials in the aldol condensation catalyst which comprise Sn or Ti as tetravalent element Y other than Si in the framework structure thereof, in which case Sn and Ti are each preferably present in the form of $SnO_2$ and $TiO_2$ in the framework structure alongside $SiO_2$. In that preferred embodiment of the present invention in which the zeolitic material comprises Sn and Ti as tetravalent element Y other than Si, and especially comprises $SnO_2$ and $TiO_2$ alongside $SiO_2$ in the framework structure thereof, it is further preferable that the framework structure does not comprise any trivalent element X other than Al. In the context of the present invention, "no element X other than Al" means that the zeolitic material has a molar ratio of X:Si in the range from 0:1 to 0.0001:1, where X is not Al, preferably from 0:1 to 0.00001:1, further preferably from 0:1 to 0.000001:1.

In principle, any trivalent element other than Al is an option for the trivalent element X. Preferably, X is selected from the group consisting of B, In, Ga, Fe, Ta and a combination of two or more thereof, and X is further preferably boron.

It is especially preferable that the framework structure of the zeolitic material in (ii) comprises $X_2O_3$ where X is B. According to the present invention, preferred zeolitic materials in the aldol condensation catalyst are those which comprise boron as trivalent element X other than Al in the form of $B_2O_3$ in the framework structure thereof. In that preferred embodiment of the present invention in which the zeolitic material comprises boron as trivalent element X other than Al, it is further preferable that the framework structure does not comprise any tetravalent element Y other than Si. In the context of the present invention, "no element Y other than Si" means that the zeolitic material has a molar ratio of Y:Si in the range from 0:1 to 0.0001:1, where X is not Si, preferably from 0:1 to 0.00001:1, further preferably from 0:1 to 0.000001:1.

In a preferred embodiment, the zeolitic material in (ii) comprises, as well as Si, O and any Al, one or more tetravalent elements Y and/or one or more trivalent elements X, additionally one or more non-framework elements Z. It is further preferable here that the zeolitic material in (ii) comprises one or more non-framework elements Z selected from the group consisting of Ti, Zr, V, Nb, Ta, Cr, Mo, W, Mn, Fe, Co, Ni, Zn, Ga, Ge, In, Sn, Pb, P, N and S. It is further preferable that the zeolitic material in (ii) comprises one or more non-framework elements Z selected from the group consisting of Zn, P, N and S. It is especially preferable that the zeolitic material in (ii) comprises one or more non-framework elements Z selected from the group consisting of Zn and P. Preferably, the zeolitic material in (ii) comprises Zn, or P, or Zn and P.

If the at least one non-framework element Z is selected from the group consisting of N, P and S or a combination thereof, it is preferably at least partly in oxidic form. It is especially preferable that N, P and S are present in the form of oxide and/or oxo anion, or in the form of oxides and/or oxo anions. According to the present invention, an oxide of N, P and S, and especially of P and S, means that the element is bonded to oxygen via one or more covalent bonds, with at least a portion of the element N, P and/or S and preferably all the valences of the element covalently bonded to oxygen. The same applies to the oxo anions of N, P and S. With regard to the oxo anions, these may in principle be in the form of the salt and/or in protonated form, it being possible in principle for salts to be formed using any suitable cation or any combination of suitable cations. Preferred cations are the cations of the alkali metals and alkaline earth metals, further preference being given to cations of the alkali metals, especially the cations of the alkali metals selected from the group consisting of Li, Na, K and combinations of two or more thereof, the salts of the oxo anions of N, P and S preferably being sodium salts. According to the present invention, preferred oxo anions of N, P and S are those which are at least partly and preferably fully protonated.

If the non-framework element Z is S, it is preferably present in the form of sulfite, sulfate, thiosulfate, dithionite, disulfite, dithionate, disulfate, or in the form of a combination of at least two thereof, further preferably in the form of sulfate and/or disulfate. It is preferably present in the form of sulfate.

If the non-framework element Z selected is P, it is preferably present in the form of $P_4O_6$, $P_2O_4$, $P_4O_{10}$, phosphinate, phosphonate, phosphate, hypodiphosphate, diphosphate and/or polyphosphate, or in the form of a combination of at least two thereof, preferably in the form of phosphate and/or diphosphate, more preferably in the form of phosphate.

Zeolites and zeolitic materials, in the context of the present application, are naturally occurring or synthetically produced materials having a three-dimensional framework structure formed from corner-linked $TO_4$ tetrahedra where T may be any tetrahedrally coordinated cation. Useful structure types for the framework structure in principle include any suitable structure type and/or any suitable combination of structure types. Useful structure types in principle for the zeolitic material thus include the structure types ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, SCO, CFI, SGF, CGS, CHA, CHI, CLO, CON, CZP, DAC, DDR, DFO, DFT, DOH, DON, EAB, EDI, EMT, EON, EPI, ERI, ESV, ETR, EUO, FAU, FER, FRA, GIS, GIU, GME, GON, GOO, HEU, IFR, IHW, ISV, ITE, ITH, ITW, IWR, IWW, JBW, KFI, LAU, LEV, LIO, LIT, LOS, LOV, LTA, LTL, LTN, MAR, MAZ, MEI, MEL, MEP, MER, MFI, MFS, MON, MOR, MOZ, MSO, MTF, MTN, MTT, MTW, MWW, NAB, NAT, NES, NON, NPO, NSI, OBW, OFF, OSI, OSO, OWE, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SOD, SOS, SSY, STF, STI, STT, TER, THO, TON, TSC, UEI, UFI, UOZ, USI, UTL, VET, VFI, VNI, VSV, WIE, WEN, YUG, ZON and mixed structures composed of two or more of these structure types.

For example, the zeolitic material may have, a structure type selected from the group consisting of AEI, AFI, BEA, CDO, CHA, FAU, FER, HEU, LEV, LTL, MEI, MFI, MEL, MOR, MTN, MWW, NON, RRO and a mixed structure composed of two or more of these structure types. Preferably, the zeolitic material in (ii) has a structure type selected from the group consisting of BEA, MFI, MWW, FAU, MOR, CHA, LEV, FER, MEL, MOR, AFI, RRO, CDO and a mixed structure composed of two or more of these structure types. Further preferably, the zeolitic material in (ii) has a structure type selected from the group consisting of BEA, MFI, MEL, MWW and a mixed structure composed of two or more of these structure types.

Preferably, the zeolitic material in (ii) has, for example, the BEA structure type. With regard to the preferred zeolitic materials of the BEA structure type, there are no restrictions with regard to the specific composition, provided that it has, if it should comprise Al, a molar Al:Si ratio in the range from 0:1 to 0.001:1. If the zeolitic material of the BEA structure type comprises one or more trivalent elements X other than Al in its framework structure, there is thus in principle no restriction with regard to the molar Si:X ratio, or with regard to the molar (Si+Y):X ratio, provided that the framework structure of the zeolitic material comprises one or more tetravalent elements Y other than Si. Therefore, the zeolitic material of the BEA structure type may in principle have a molar (Si+Y):X ratio, for example, in the range from 2:1 to 1000:1, the zeolitic material having the BEA structure type preferably having a molar (Si+Y):X ratio of 2:1 to 500:1.

Further preferably, the zeolitic material having the BEA structure type has a molar (Si+Y):X ratio of 2:1 to 350:1, further preferably of 2:1 to 250:1, further preferably of 2:1 to 150:1, further preferably of 2:1 to 50:1, further preferably of 8:1 to 17:1.

In addition, there are no restrictions in principle with regard to the trivalent elements X other than Al which may be present in the preferred zeolitic materials of the BEA structure type, and so this may be any suitable trivalent element X or a combination of two or more thereof. Therefore, the preferred zeolitic materials of the BEA structure type may comprise one or more trivalent elements X other than Al, selected from the group consisting of B, In, Ga, Fe, Ta and a combination of two or more thereof. According to the present invention, it is especially preferable that the zeolitic material of the BEA structure type comprises B as trivalent element X other than Al, it being further preferable to use, as zeolitic material, B-BEA which, aside from boron, does not comprise any further trivalent element X other than Al. In this particularly preferred embodiment of the present invention, with regard to the zeolitic material of the BEA structure type, it is further preferable that the framework structure thereof does not comprise any tetravalent element Y other than Si.

According to the present invention, it is equally preferable that the preferred zeolitic material of the BEA structure type does not comprise any trivalent element X other than Al and hence comprises one or more tetravalent elements Y other than Si. With regard to the tetravalent element Y other than Si which is present alongside Si in the framework structure of the zeolitic material of the BEA structure type, there is no restriction in principle, and so any suitable tetravalent element Y other than Si may be present therein. In these preferred embodiments of the present invention, Y is preferably selected from the group consisting of Sn, Ti, Zr, Ge and a combination of two or more thereof, Y further preferably being selected from the group consisting of Sn, Ti, Ge and a combination thereof, and further preferably from the group consisting of Sn, Ti and a combination thereof. According to the present invention, it is especially preferable that the zeolitic material of the BEA structure type does not comprise any trivalent element X other than Al and comprises Sn as tetravalent element Y other than Si in its framework structure. In this particularly preferred embodiment of the present invention, with regard to the zeolitic material of the BEA structure type, it is further preferable that the framework structure thereof does not comprise any tetravalent element Y other than Si apart from Sn.

Equally preferably, the zeolitic material in (ii) has, for example, the MFI, MEL structure type, or a mixed structure composed of these two structure types, and further preferably a mixed MFI/MEL structure. With regard to the preferred zeolitic materials of the mixed MFI/MEL structure type, there are no restrictions with regard to the specific composition, provided that they have, if they should comprise Al, a molar Al:Si ratio in the range from 0:1 to 0.001:1. If the zeolitic material of the mixed MFI/MEL structure type comprises one or more trivalent elements X other than Al in its framework structure, there is thus in principle no restriction with regard to the molar Si:X ratio, or with regard to the molar (Si+Y):X ratio, provided that the framework structure of the zeolitic material comprises one or more tetravalent elements Y other than Si. Therefore, the zeolitic material of the mixed MFI/MEL structure type may in principle have a molar (Si+Y):X ratio, for example, in the range from 2:1 to 1000:1, this zeolitic material having a mixed MFI/MEL structure type preferably having a molar (Si+Y):X ratio of 2:1 to 500:1. Further preferably, this zeolitic material having a mixed MFI/MEL structure type has a molar (Si+Y):X ratio of 2:1 to 350:1, further preferably of 2:1 to 250:1, further preferably of 2:1 to 150:1, further preferably of 2:1 to 50:1. Therefore, the zeolitic material in (ii) having a mixed MFI/MEL structure type has a molar (Si+Y):X ratio in the range from 2:1 to 50:1.

With regard to the trivalent elements X other than Al which may be present in the preferred zeolitic materials of the mixed MFI/MEL structure type, there are likewise no restrictions in principle, and so this may be any suitable trivalent element X or combinations of two or more thereof. Therefore, the preferred zeolitic materials of the mixed MFI/MEL structure type may comprise one or more trivalent elements X other than Al, selected from the group consisting of B, In, Ga, Fe, Ta and a combination of two or more thereof. According to the present invention, it is especially preferable that the zeolitic material of the mixed MFI/MEL structure type comprises B as trivalent element X other than Al, it being especially preferable to use, as zeolitic material, ZBM-11 which, aside from boron, does not comprise any further trivalent element X other than Al. In this particularly preferred embodiment of the present invention, with regard to the zeolitic material of the mixed MFI/MEL structure type, it is further preferable that the framework structure thereof does not comprise any tetravalent element Y other than Si.

Equally preferably, the zeolitic material has, for example, the MFI structure type. With regard to the preferred zeolitic materials of the MFI structure type, there are likewise no restrictions with regard to the specific composition, provided that it has, if it should comprise Al, a molar Al:Si ratio in the range from 0:1 to 0.001:1. If the zeolitic material of the MFI structure type comprises one or more trivalent elements X other than Al in its framework structure, there is thus in principle no restriction with regard to the molar Si:X ratio, or with regard to the molar (Si+Y):X ratio, provided that the framework structure of the zeolitic material comprises one or more tetravalent elements Y other than Si. According to the present invention, it is further preferable that the preferred zeolitic material of the MFI structure type does not comprise any trivalent element X other than Al and hence comprises one or more tetravalent elements Y other than Si. With regard to the tetravalent element Y other than Si which is present alongside Si in the framework structure of the zeolitic material of the MFI structure type, there is no restriction in principle, and so any suitable tetravalent element Y other than Si may be present therein. In these preferred embodiments of the present invention, Y is again preferably selected from the group consisting of Sn, Ti, Zr, Ge and a combination of two or more thereof, Y further preferably being selected from the group consisting of Sn, Ti, Ge and a combination thereof, and further preferably from the group consisting of Sn, Ti and a combination thereof. According to the present invention, it is especially preferable that the zeolitic material of the MFI structure type does not comprise any trivalent element X other than Al and comprises Sn or Ti as tetravalent element Y other than Si in its framework structure. In this particularly preferred embodiment of the present invention, with regard to the zeolitic material of the MFI structure type, it is further preferable that the framework structure thereof, apart from Sn or Ti, does not comprise any further tetravalent element Y other than Si, the zeolitic material more preferably comprising Sn-MFI and/or TS-1, further preferably Sn-MFI or TS-1.

Equally preferably, the zeolitic material in (ii) has, for example, the MWW structure type. With regard to the preferred zeolitic materials of the MWW structure type, there are no restrictions with regard to the specific composition, provided that it has, if it should comprise Al, a molar Al:Si ratio not exceeding 0.001:1. If the zeolitic material of the MWW structure type comprises one or more trivalent elements X other than Al in its framework structure, there is thus in principle no restriction with regard to the molar Si:X ratio, or with regard to the molar (Si+Y):X ratio, provided that the framework structure of the zeolitic material comprises one or more tetravalent elements Y other than Si. Therefore, the zeolitic material of the MWW structure type may in principle have a molar (Si+Y):X ratio in the range, for example, from 2:1 to 1000:1, this zeolitic material having the MWW structure type preferably having a molar (Si+Y):X ratio of 2:1 to 500:1, further preferably of 2:1 to 350:1, further preferably of 2:1 to 250:1, further preferably of 2:1 to 150:1, further preferably of 2:1 to 50:1. Therefore, the zeolitic material in (ii) preferably has the MWW structure type and a molar (Si+Y):X ratio in the range from 2:1 to 500:1.

In addition, there are no restrictions in principle with regard to the trivalent elements X other than Al which may be present in the preferred zeolitic materials of the MWW structure type, and so this may comprise any suitable trivalent element X or combinations of two or more thereof. Therefore, the preferred zeolitic materials of the MWW structure type may comprise one or more trivalent elements X other than Al, selected from the group consisting of B, In, Ga, Fe, Ta and a combination of two or more thereof. According to the present invention, it is especially preferable that the zeolitic material of the MWW structure type comprises B as trivalent element X other than Al, it being further preferable to use, as zeolitic material, B-MWW which, aside from boron, does not comprise any further trivalent element X other than Al. In this particularly preferred embodiment of the present invention, with regard to the zeolitic material of the MWW structure type, it is further preferable that the framework structure thereof does not comprise any tetravalent element Y other than Si.

According to the present invention, it is further preferable that the preferred zeolitic material of the MWW structure type does not comprise any trivalent element X other than Al and hence comprises one or more tetravalent elements Y other than Si. With regard to the tetravalent element Y other than Si which is present alongside Si in the framework structure of the zeolitic material of the MWW structure type, there is no restriction in principle, and so any suitable tetravalent element Y other than Si may be present therein. In these preferred embodiments of the present invention, Y is preferably selected from the group consisting of Sn, Ti, Zr, Ge and a combination of two or more thereof, Y further preferably being selected from the group consisting of Sn, Ti, Ge and a combination thereof, and further preferably from the group consisting of Sn, Ti and a combination thereof. According to the present invention, it is especially preferable that the zeolitic material of the MWW structure type does not comprise any trivalent element X other than Al and comprises Sn or Ti as tetravalent element Y other than Si in its framework structure. In this particularly preferred embodiment of the present invention, with regard to the zeolitic material of the MWW structure type, it is further preferable that the framework structure thereof, apart from Sn or Ti, does not comprise any further tetravalent element Y other than Si, the zeolitic material more preferably comprising Sn-MWW and/or Ti-MWW, further preferably Sn-MWW or Ti-MWW.

The zeolitic material having the MWW structure type is unrestricted with regard to possible non-framework elements Z and may thus in principle comprise any non-framework element Z. Preferably, the zeolitic material having the MWW structure type comprises one or more non-framework elements Z selected from the group consisting of Ti, Zr, V, Nb, Ta, Cr, Mo, W, Mn, Fe, Co, Ni, Zn, Ga, Ge, In, Sn, Pb, P, N and S, preferably consisting of Zn, P, N and S, further preferably consisting of Zn and P. More preferably, the zeolitic material having the MWW structure type comprises Zn as non-framework element Z, the zeolitic material more preferably comprising ZnTi-MWW. It is also preferable that the zeolitic material having the MWW structure type has a molar (Si+Y):X ratio in the range from 2:1 to 500:1, preferably from 2:1 to 50:1, and comprises Zn as non-framework element Z.

In principle, it is possible that the zeolitic material in (ii) comprises alkali metals and/or alkaline earth metals as well as the one or more non-framework elements Z. In principle, it is possible that the zeolitic material in (ii) comprises Li, Na, K, Rb, Cs, Be, Mg, Ca, Sr, Ca or a combination of two or more thereof. Preferably, the total content of alkali metal and alkaline earth metal in the zeolitic material in (ii), calculated as alkali metal oxide ($M_2O$) and alkaline earth metal oxide (MO), is in the range from 0% to 1% by weight, preferably from 0% to 0.1% by weight, further preferably from 0% to 0.05% by weight, further preferably from 0% to 0.01% by weight. Further preferably, the total content of alkali metal and alkaline earth metal in the zeolitic material in (ii), calculated as alkali metal oxide ($M_2O$) and alkaline earth metal oxide (MO), is in the range from 0% to 0.005% by weight, further preferably in the range from 0% to 0.001% by weight, further preferably in the range from 0% to 0.0001% by weight, based in each case on the total weight of the zeolitic material. More preferably, the zeolitic material in (ii) is free of alkali metals and alkaline earth metals. "Free of alkali metals and alkaline earth metals" in this context of the present invention means that alkali metals and alkaline earth metals are present in the zeolitic material in (ii) only in traces, i.e. in the form of an impurity at most, if at all.

The zeolitic material used in the process according to the invention, which is present in the aldol condensation catalyst, aside from its composition as described here with regard to the particular and preferred embodiments thereof, is in principle not subject to any further restrictions at all, especially with regard to its chemical and physical properties, unless these automatically arise from the composition and structure thereof.

Therefore, the zeolitic material used in the aldol condensation catalyst is not restricted in principle, for example, with regard to its acid-base properties, provided that the reaction of the formaldehyde source with acetic acid to give acrylic acid can be at least partly assured. According to the present invention, the zeolitic material, however, preferably has acid sites, these comprising Brønsted and/or Lewis acid sites. Accordingly, the zeolitic material preferably has one or more desorption maxima in its desorption spectrum obtained by temperature-programmed desorption with $NH_3$ ($NH_3$-TPD).

Preferably, the zeolitic material in (ii) thus has a desorption maximum within at least one of the temperature ranges of 0 to 250° C., 251 to 500° C. and 501 to 700° C. in a temperature-programmed desorption with $NH_3$. It is therefore preferable that the zeolitic material present in (ii) in the aldol condensation catalyst has a desorption maximum within the temperature range of 0 to 250° C. and/or within the temperature range of 251 to 500° C. and/or within the temperature range of 501 to 700° C.

With regard to the intensity of the one or more desorption maxima preferably present in the desorption spectrum of the zeolitic material obtained by $NH_3$-TPD, there are no restrictions at all in principle, and so the relative amount of acidic sites in the zeolitic material is not subject to any restrictions in principle. According to the present invention, it is preferable that, after deconvolution of the desorption spectrum, the desorption maximum within the temperature range of 0 to 250° C. has a concentration of desorbed $NH_3$ in the range from 0.001 to 1.0 mmol/g and/or the desorption maximum within the temperature range of 251 to 500° C. has a concentration of desorbed $NH_3$ in the range from 0.001 to 0.5 mmol/g and/or the desorption maximum within the temperature range of 501 to 700° C. has a concentration of desorbed $NH_3$ in the range from 0.001 to 0.1 mmol/g, where the concentration of desorbed $NH_3$ in mmol is based on the mass of the zeolitic material in g.

Further preferably, after deconvolution of the desorption spectrum, the desorption maximum within the temperature range of 0 to 250° C. has a concentration of desorbed $NH_3$ in the range from 0.0025 to 0.9 mmol/g, further preferably in the range from 0.005 to 0.75 mmol/g, further preferably in the range from 0.01 to 0.5 mmol/g, further preferably in the range from 0.025 to 0.4 mmol/g. Equally further preferably, after deconvolution of the desorption spectrum, the desorption maximum within the temperature range of 251 to 500° C. has a concentration of desorbed $NH_3$ in the range from 0.005 to 0.25 mmol/g, further preferably in the range from 0.0075 to 0.1 mmol/g, further preferably in the range from 0.01 to 0.08 mmol/g. Equally further preferably, after deconvolution of the desorption spectrum, the desorption maximum within the temperature range of 501 to 700° C. has a concentration of desorbed $NH_3$ in the range from 0.002 to 0.075 mmol/g, further preferably from 0.005 to 0.05 mmol/g.

Independently of this, the zeolitic material present in the aldol condensation catalyst is preferably characterized by its IR spectrum. More particularly, this preferably has at least one maximum of an absorption band within at least one of the wavenumber ranges from 3790 to 3691 $cm^{-1}$, 3690 to 3591 $cm^{-1}$ and 3590 to 3490 $cm^{-1}$.

Moreover, the zeolitic material present in the aldol condensation catalyst, independently of this, is preferably characterized by its hydrophilic/hydrophobic properties, which are reflected in its ability to absorb water. More particularly, the zeolitic material preferably features a water absorption in the range from 1% to 50% by weight, preferably in the range from 2% to 20% by weight. In the context of the present invention, the water absorption is based on the relative amount of water which is absorbed by the zeolitic material, proceeding from its dry weight up to a relative humidity of the ambient air of 85% at 25° C. According to the present invention, the water absorption measured for the zeolitic material is preferably based on the process for determination thereof described in the experimental section.

With regard to the specific surface area thereof, the zeolitic material present in the aldol condensation catalyst is not subject to any restrictions at all, and so it may in principle have any conceivable specific surface area. According to the present invention, the zeolitic material in (ii) preferably has a specific BET surface area, determined to DIN 66131, in the range from 250 to 650 $m^2/g$, further preferably from 300 to 580 $m^2/g$. Further preferably, the zeolitic material in (ii) has a specific BET surface area in the range from 360 to 540 $m^2/g$.

With regard to the aldol condensation catalyst used in the process according to the invention, there is no restriction at all in principle with regard to the constituents present therein, provided that it comprises a zeolitic material wherein the framework structure comprises Si and O, and such a small amount of Al, if any, that the molar Al:Si ratio of aluminum to silicon thereof does not exceed 0.001:1. Therefore, it is possible in principle that the aldol condensation catalyst in (ii) also comprises vanadium. It is preferable that the aldol condensation catalyst in (ii), outside the framework structure of the zeolitic material present therein, comprises from 0% to 1% by weight of vanadium, calculated as vanadium(V) oxide and based on the total weight of the aldol condensation catalyst. Consequently, the vanadium content of the aldol condensation catalyst in (ii), outside the framework structure of the zeolitic material present therein, may in principle assume any value not exceeding 1% by weight of vanadium, calculated as vanadium(V) oxide and based on the total weight of the aldol condensation catalyst. Preferably, the aldol condensation catalyst in (ii) comprises, outside the framework structure of the zeolitic material present therein, from 0% to 0.1% by weight, further preferably from 0% to 0.01% by weight, further preferably from 0% to 0.001% by weight, further preferably from 0% to 0.0001% by weight, of vanadium, calculated as vanadium (V) oxide and based on the total weight of the aldol condensation catalyst. More preferably, the aldol condensation catalyst in (ii), outside the framework structure of the zeolitic material present therein, is free of vanadium. The expression "free of vanadium" in the context of the present invention likewise means that vanadium is present only in traces, i.e. in the form of an impurity at most, if at all.

It is preferable that the aldol condensation catalyst in (ii) comprises a total of not more than 1% by weight of vanadium, based on vanadium, as vanadium(V) oxide. It is further preferable that the aldol condensation catalyst in (ii) comprises a total of from 0% to 1% by weight, preferably from 0% to 0.1% by weight, further preferably from 0% to 0.01% by weight, further preferably from 0% to 0.001% by weight, further preferably from 0% to 0.0001% by weight, of vanadium, calculated as vanadium(V) oxide and based on the total weight of the aldol condensation catalyst. More preferably, the aldol condensation catalyst in (ii) is totally free of vanadium. "Free of vanadium" in the context of the present invention means that vanadium is present in the aldol condensation catalyst only in traces, i.e. in the form of an impurity at most, if at all.

It is additionally preferable that the aldol condensation catalyst in (ii) comprises a binder material in addition to the zeolitic material in (ii). Possible binder materials include all the materials which are known to those skilled in the art and can be used here as binder material, and which affect the catalyst only to a minor degree or only to the degree of the resulting dilution of the catalyst, if at all.

Preferably, the binder material is selected from the group consisting of graphite, $SiO_2$, $TiO_2$, $ZrO_2$, MgO, combinations of two or more thereof and mixed oxides of at least two elements selected from the group consisting of Si, Ti, Zr, and Mg, and combinations of two or more thereof. The weight ratio of the zeolitic material in (ii) to the binder material is not subject to any restrictions in principle. In general, the weight ratio of the zeolitic material in (ii) to the binder material may be in the range from 20:1 to 1:20, preferably from 10:1 to 1:10, further preferably from 1:1 to 1:10.

The aldol condensation catalyst in (ii) may, as well as the zeolitic material in (ii) and the binder material, also comprise further components, possible options here being supports or else further catalytically active components. Preferably, the aldol condensation catalyst in (ii) consists of zeolitic material and any binder material to an extent of 30% to 100% by weight, further preferably to an extent of 50% to 100% by weight, further preferably to an extent of 70% to 100% by weight, further preferably to an extent of 80% to 100% by weight, further preferably to an extent of 90% to 100% by weight, further preferably to an extent of 95% to 100% by weight, further preferably to an extent of 98% to 100% by weight, further preferably to an extent of 99% to 100% by weight.

The aldol condensation catalyst in (ii) may be in any form suitable for the performance of the process according to the invention. Consequently, the aldol condensation catalyst in (ii) may be in powder form, in the form of spray powder, or in the form of spray granules. Equally, the aldol condensation catalyst may be in the form of shaped bodies. If the aldol condensation catalyst is in the form of shaped bodies, it is preferably shaped to extrudates, preferably having a rectangular, triangular, hexagonal, square, oval or circular cross section, or is in a star shape, in tablet form, in the form of spheres, or in the form of hollow cylinders. Equally possible is a combination of two or more of the aforementioned forms.

Process Parameters

In step (ii) of the process according to the invention, stream S4 is contacted with the aldol condensation catalyst comprising a zeolitic material to obtain stream S6 comprising acrylic acid. Stream S4 may be present here completely in gaseous form, completely in liquid form or in a form in which at least one component is in gaseous form and at least one component in liquid form. Preferably, stream S4 in step (ii) is completely in gaseous form.

In principle, the present process can be conducted at all temperatures at which a stream S6 comprising acrylic acid is obtained with the aid of the process comprising steps (i) and (ii). Preferably, the contacting in (ii) is effected at a temperature in the range from 200 to 400° C., further preferably from 220 to 380° C. Further preferably, the contacting in (ii) is effected at a temperature in the range from 230 to 370° C., further preferably from 240 to 360° C., further preferably from 250 to 350° C. This temperature should be understood as the highest temperature of the gas phase in the reactor used for the reaction in (ii), measured with an unprotected Pt-100 thermocouple.

In principle, the present process can be conducted at all pressures at which a stream S6 comprising acrylic acid is obtained with the aid of the process comprising steps (i) and (ii). Preferably, the contacting in (ii) is effected at a pressure from 0.01 to 10 bar, further preferably from 0.02 to 7.5 bar, further preferably from 0.05 to 5 bar. Further preferably, the contacting in (ii) is effected at a pressure from 0.1 to 3.5 bar, further preferably from 0.5 to 2.5 bar, further preferably from 0.75 to 2.0 bar, further preferably from 0.9 to 1.5 bar. All pressures in the context of the present invention should be understood as absolute pressures.

Preferably, the contacting in (ii) of the process according to the invention is effected at a temperature in the range from 200 to 400° C., further preferably from 220 to 380° C., further preferably from 230 to 370° C., further preferably from 240 to 360° C., further preferably from 250 to 350° C., and a pressure of 0.01 to 10 bar, further preferably of 0.02 to 7.5 bar, further preferably of 0.05 to 5 bar, further preferably of 0.1 to 3.5 bar, further preferably of 0.5 to 2.5 bar, further preferably of 0.75 to 2.0 bar, further preferably of 0.9 to 1.5 bar. More preferably, the contacting in (ii) of the process according to the invention is effected at a temperature in the range from 200 to 400° C. and a pressure of 0.01 to 10 bar, more preferably at a temperature in the range from 250 to 350° C. and a pressure of 0.5 to 2.5 bar.

The space velocity (gas hourly space velocity, GHSV) with respect to the contacting in (ii) of the process according to the invention is preferably chosen such that an advantageous balance of conversion, selectivity, yield, reactor geometry, reactor dimensions and process regime is obtained. In the context of the present invention, the space velocity is understood to mean the ratio of the volume flow rate S4 with the unit (volume/time) to the volume of the aldol condensation catalyst in (ii); the space velocity therefore has the unit (1/time).

Preferably, the space velocity in the present process is in the range from 50 to 10 000 $h^{-1}$, preferably from 70 to 7500 $h^{-1}$, further preferably from 90 to 5000 $h^{-1}$, further preferably from 100 to 2500 $h^{-1}$, further preferably from 150 to 2000 $h^{-1}$, in each case at a pressure of 101.325 kPa and a temperature of 0° C.

A further important process parameter in the context of the present invention is the space-time yield (STY). In the context of the present invention, the space-time yield is understood to mean the ratio of the mass flow rate of acrylic acid in stream S6 with the unit (mass/time) to the mass of the aldol condensation catalyst in (ii); the space-time yield therefore has the unit (mass/mass/time).

Preferably, the space-time yield in the present process is in the range from 0.01 to 2.5 kg/kg/h, further preferably from 0.025 to 2.0 kg/kg/h, further preferably 0.05 to 1.75 kg/kg/h.

Further Steps

The process according to the invention may comprise one or more further steps in addition to steps (i) and (ii). Preferably, the process according to the invention additionally comprises, as step (iii), the regenerating of the aldol condensation catalyst in (ii).

The regenerating in (iii) is preferably conducted at a temperature in the range from 300 to 700° C., further preferably from 350 to 600° C. The regenerating in (iii) is preferably conducted over a period of 1 to 48 hours, further preferably of 10 to 40 hours, further preferably 20 to 30 hours, further preferably of 22 to 26 hours. The regenerating in (iii) is preferably conducted in the presence of oxygen. Therefore, the regenerating in (iii) can be conducted in the presence of pure oxygen or else in the presence of a gas mixture comprising oxygen. It is preferable that the regenerating in (iii) is conducted in the presence of a gas mixture of oxygen and an inert gas, the inert gas preferably being nitrogen. Therefore, the regenerating in (iii) is preferably conducted in the presence of a gas mixture of oxygen and nitrogen. Therefore, step (iii) is preferably conducted at a temperature in the range from 350 to 600° C. in the presence of a gas mixture of oxygen and nitrogen.

The space velocity (gas hourly space velocity, GHSV) with respect to the regenerating in (iii) of the process according to the invention may assume any value at which regeneration of the aldol condensation catalyst in (ii) is achieved. Preferably, the space velocity with respect to the regenerating is in the range from 50 to 10 000 $h^{-1}$, preferably from 100 to 7500 $h^{-1}$, further preferably from 75 to 5000 $h^{-1}$, further preferably from 100 to 2500 $h^{-1}$.

The present invention is illustrated in detail by the following embodiments and combinations of embodiments which are apparent from the dependency references and other references:

1. A process for preparing acrylic acid, comprising
   (i) providing a stream S4 comprising a formaldehyde source and acetic acid;
   (ii) contacting the stream S4 with an aldol condensation catalyst comprising a zeolitic material to obtain a stream S6 comprising acrylic acid;
   wherein the framework structure of the zeolitic material in (ii) includes Si and O, and has a molar Al:Si ratio within the range from 0:1 to 0.001:1, preferably from 0:1 to 0.0001:1, further preferably from 0:1 to 0.00001:1;
   and wherein the framework structure of the zeolitic material in (ii), in addition to Si and any Al, comprises one or more elements selected from the group consisting of tetravalent elements Y other than Si and trivalent elements X other than Al.

2. The process according to embodiment 1, wherein the framework structure of the zeolitic material in (ii) comprises $YO_2$ where Y is preferably selected from the group consisting of Sn, Ti, Zr, Ge, V and a combination of two or more thereof, further preferably from the group consisting of Sn, Ti, Ge and a combination of two or more thereof, further preferably from the group consisting of Sn, Ti and a combination thereof.

3. The process according to embodiment 1 or 2, wherein the framework structure of the zeolitic material in (ii) comprises $X_2O_3$ where X is preferably selected from the group consisting of B, In, Ga, Fe, Ta and a combination of two or more thereof, where X is further preferably B.

4. The process according to any of embodiments 1 to 3, wherein the zeolitic material in (ii) comprises one or more non-framework elements Z selected from the group consisting of Ti, Zr, V, Nb, Ta, Cr, Mo, W, Mn, Fe, Co, Ni, Zn, Ga, Ge, In, Sn, Pb, P, N and S, preferably from the group consisting of Zn, P, N and S, further preferably from the group consisting of Zn and P.

5. The process according to embodiment 4, wherein N, P and S, preferably P, are present at least partly in oxidic form, preferably as oxide and/or oxo anion.

6. The process according to any of embodiments 1 to 5, wherein the zeolitic material in (ii) has a structure type selected from the group consisting of BEA, MFI, MWW, FAU, MOR, CHA, LEV, FER, MEL, MOR, AFI, RRO, CDO and a mixed structure composed of two or more of these structure types.

7. The process according to any of embodiments 1 to 6, wherein the zeolitic material in (ii) is of the BEA structure type.

8. The process according to embodiment 7, wherein the zeolitic material in (ii) has a molar (Si+Y):X ratio in the range from 2:1 to 500:1, preferably from 2:1 to 50:1.

9. The process according to any of embodiments 1 to 6, wherein the zeolitic material in (ii) has the MFI or MEL structure type or a mixed structure composed of these structure types.

10. The process according to embodiment 9, wherein the zeolitic material in (ii) has a molar (Si+Y):X ratio in the range from 2:1 to 500:1, preferably from 2:1 to 50:1.

11. The process according to any of embodiments 1 to 6, wherein the zeolitic material in (ii) is of the MWW structure type.

12. The process according to embodiment 11, wherein the zeolitic material in (ii) has a molar (Si+Y):X ratio in the range from 2:1 to 500:1.

13. The process according to embodiment 11 or 12, wherein the zeolitic material in (ii) comprises Zn as a non-framework element.

14. The process according to any of embodiments 1 to 13, wherein the total content of alkali metal and alkaline earth metal in the zeolitic material in (ii), calculated as alkali metal oxide ($M_2O$) and alkaline earth metal oxide (MO), is from 0% to 0.1% by weight, preferably from 0% to 0.05% by weight, further preferably from 0% to 0.01% by weight, further preferably from 0% to 0.001% by weight, based in each case on the total weight of the zeolitic material.

15. The process according to any of embodiments 1 to 14, wherein the aldol condensation catalyst in (ii) comprises a binder material in addition to the zeolitic material in (ii).

16. The process according to embodiment 15, wherein the binder material is selected from the group consisting of graphite, $SiO_2$, $TiO_2$, $ZrO_2$, MgO, combinations of two or more thereof and mixed oxides of at least two elements selected from the group consisting of Si, Ti, Zr, Mg and combinations of two or more thereof, preferably selected from the group consisting of graphite, $SiO_2$, $TiO_2$ and $ZrO_2$, combinations of two or more thereof and mixed oxides of at least two elements selected from the group consisting of Si, Ti, Zr and combinations of two or more thereof.

17. The process according to any of embodiments 1 to 16, wherein the aldol condensation catalyst is in the form of shaped bodies, preferably shaped to extrudates, preferably having a rectangular, triangular, hexagonal, square, oval or circular cross section, or is in a star shape, in tablet form, in the form of spheres, or in the form of hollow cylinders.

18. The process according to any of embodiments 1 to 17, wherein the molar ratio of acetic acid to formaldehyde, obtained and/or obtainable from the formaldehyde source, in stream S4 is in the range from 0.01:1 to 10:1, preferably from 1:1 to 8:1, preferably from 1.5:1 to 5:1, further preferably from 2:1 to 4.4:1, further preferably from 2.5:1 to 4.1:1.

19. The process according to any of embodiments 1 to 18, wherein stream S4 is brought to a temperature in the range from 150 to 250° C., preferably from 180 to 220° C., before being contacted in (ii).

20. The process according to any of embodiments 1 to 19, wherein the contacting in (ii) is effected at a temperature in the range from 200 to 400° C., preferably from 230 to 370° C., further preferably from 250 to 350° C.

21. The process according to any of embodiments 1 to 20, wherein the contacting in (ii) is effected at a pressure in the range from 0.01 to 10 bar, preferably from 0.05 to 5 bar, preferably from 0.1 to 3.5 bar, further preferably from 0.5 to 2.5 bar.

22. The process according to any of embodiments 1 to 21, wherein the contacting in (ii) is effected at a space velocity (GHSV) in the range from 50 to 10 000 $h^{-1}$, preferably from 70 to 7500 $h^{-1}$, further preferably from 90 to 5000 $h^{-1}$, preferably from 100 to 2500 $h^{-1}$, further preferably from 150 to 2000 $h^{-1}$.

23. The process according to any of embodiments 1 to 22, wherein the space-time yield in the contacting in (ii) is in the range from 0.01 to 2.5 kg/kg/h, preferably from 0.025 to 2.0 kg/kg/h, further preferably 0.05 to 1.75 kg/kg/h, the space-time yield being defined as kg(acrylic acid)/kg (aldol condensation catalyst)/h.

24. The process according to any of embodiments 1 to 23, wherein stream S4 additionally comprises one or more diluents, preferably selected from the group consisting of nitrogen, carbon monoxide, carbon dioxide, ethene, acetone, water and a combination of two or more thereof.
25. The process according to any of embodiments 1 to 24, wherein the formaldehyde source in (i) is an anhydrous formaldehyde source, preferably selected from the group consisting of trioxane and paraformaldehyde.
26. The process according to any of embodiments 1 to 25, wherein the temperature-programmed desorption with $NH_3$ (NH3TPD) of the zeolitic material in (ii) has a desorption maximum within at least one of the temperature ranges of 0 to 250° C., 251 to 500° C. and 501 to 700° C., wherein following deconvolution of the desorption spectrum the desorption maximum in the temperature range of 0 to 250° C. has a concentration of desorbed $NH_3$ in the range from 0.001 to 1.0 mmol/g, the desorption maximum in the temperature range of 251 to 500° C. a concentration of desorbed $NH_3$ in the range from 0.001 to 0.5 mmol/g, and the desorption maximum in the temperature range 501 to 700° C. a concentration of desorbed $NH_3$ in the range from 0.001 to 0.1 mmol/g, where the concentration of desorbed $NH_3$ is defined as mmol(desorbed $NH_3$)/g(zeolitic material).
27. The process according to any of embodiments 1 to 26, wherein the IR spectrum of the zeolitic material in (ii) has at least one maximum of an absorption band within at least one of the wavenumber ranges from 3790 to 3691 $cm^{-1}$, 3690 to 3591 $cm^{-1}$ and 3590 to 3490 $cm^{-1}$.
28. The process according to any of embodiments 1 to 27, wherein the zeolitic material in (ii) has a water absorption in the range from 1% to 50% by weight, preferably in the range from 2% to 20% by weight.
29. The process according to any of embodiments 1 to 28, wherein the aldol condensation catalyst in (ii) comprises, outside the framework structure of the zeolitic material present in the aldol condensation catalyst, from 0% to 1% by weight, preferably from 0% to 0.1% by weight, further preferably from 0% to 0.01% by weight, further preferably from 0% to 0.001% by weight, further preferably from 0% to 0.0001% by weight, of vanadium, calculated as vanadium(V) oxide and based on the total weight of the aldol condensation catalyst.
30. The process according to any of embodiments 1 to 29, wherein the aldol condensation catalyst in (ii) comprises from 0% to 1% by weight, preferably from 0% to 0.1% by weight, further preferably from 0% to 0.01% by weight, further preferably from 0% to 0.001% by weight, further preferably from 0% to 0.0001% by weight, of vanadium, calculated as vanadium(V) oxide and based on the total weight of the aldol condensation catalyst.
31. The process according to any of embodiments 1 to 24, additionally comprising
    (iii) regenerating the aldol condensation catalyst in (ii), the regenerating preferably being conducted at a temperature in the range from 300 to 700° C., further preferably from 350 to 600° C., the regenerating preferably being conducted in the presence of oxygen, further preferably in the presence of a mixture of oxygen and an inert gas, further preferably in the presence of a mixture of oxygen and nitrogen.
32. A stream S6 obtainable or obtained by a process according to any of embodiments 1 to 30.

Figure 1:
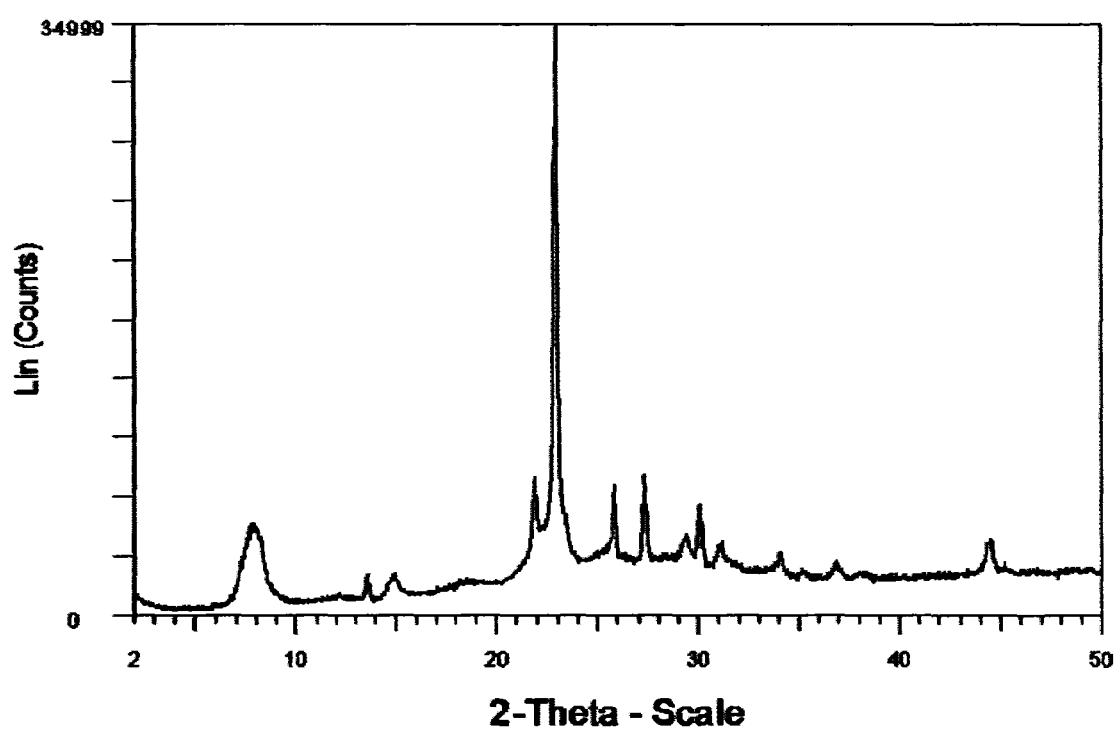
FIG. 1 shows the x-ray diffractogram of the zeolitic material according to example 1. Plotted on the abscissa is the angle (2 theta/°), with explicit values, from left to right, of 2, 10, 20, 30, 40 and 50. Plotted on the ordinate is the signal intensity (Lin (counts)), with explicit values, from bottom to top, of 0 and 34 999.
Figure 2:
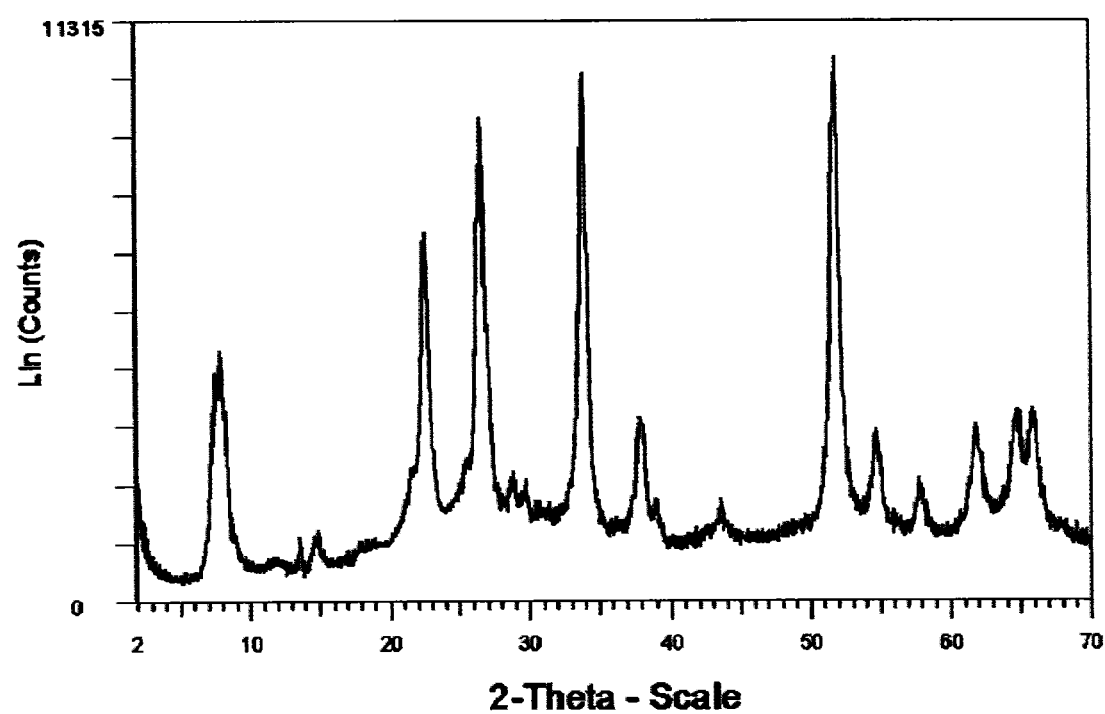
FIG. 2 shows the x-ray diffractogram of the zeolitic material according to example 2. Plotted on the abscissa is the angle (2 theta/°), with explicit values, from left to right, of 2, 10, 20, 30, 40, 50, 60 and 70. Plotted on the ordinate is the signal intensity (Lin (counts)), with explicit values, from bottom to top, of 0 and 11 315.
Figure 3:
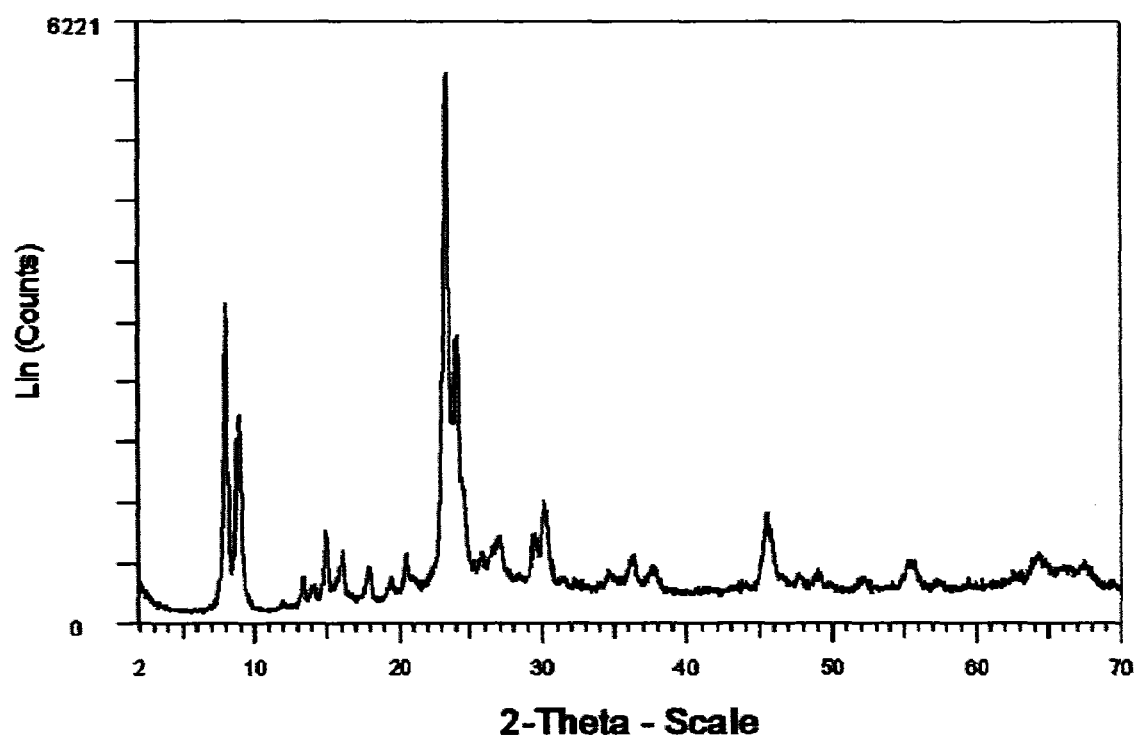
FIG. 3 shows the x-ray diffractogram of the zeolitic material according to example 3. Plotted on the abscissa is the angle (2 theta/°), with explicit values, from left to right, of 2, 10, 20, 30, 40, 50, 60 and 70. Plotted on the ordinate is the signal intensity (Lin (counts)), with explicit values, from bottom to top, of 0 and 6221.
Figure 4:
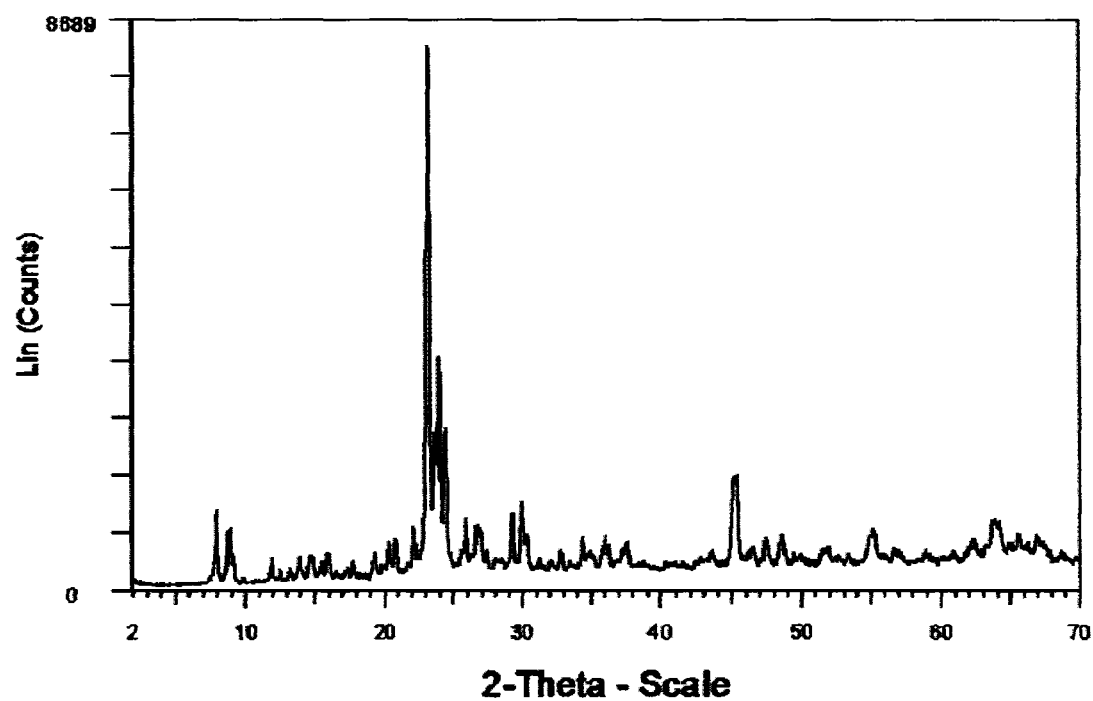
FIG. 4 shows the x-ray diffractogram of the zeolitic material according to example 4. Plotted on the abscissa is the angle (2 theta/°), with explicit values, from left to right, of 2, 10, 20, 30, 40, 50, 60 and 70. Plotted on the ordinate is the signal intensity (Lin (counts)), with explicit values, from bottom to top, of 0 and 8689.
Figure 5:
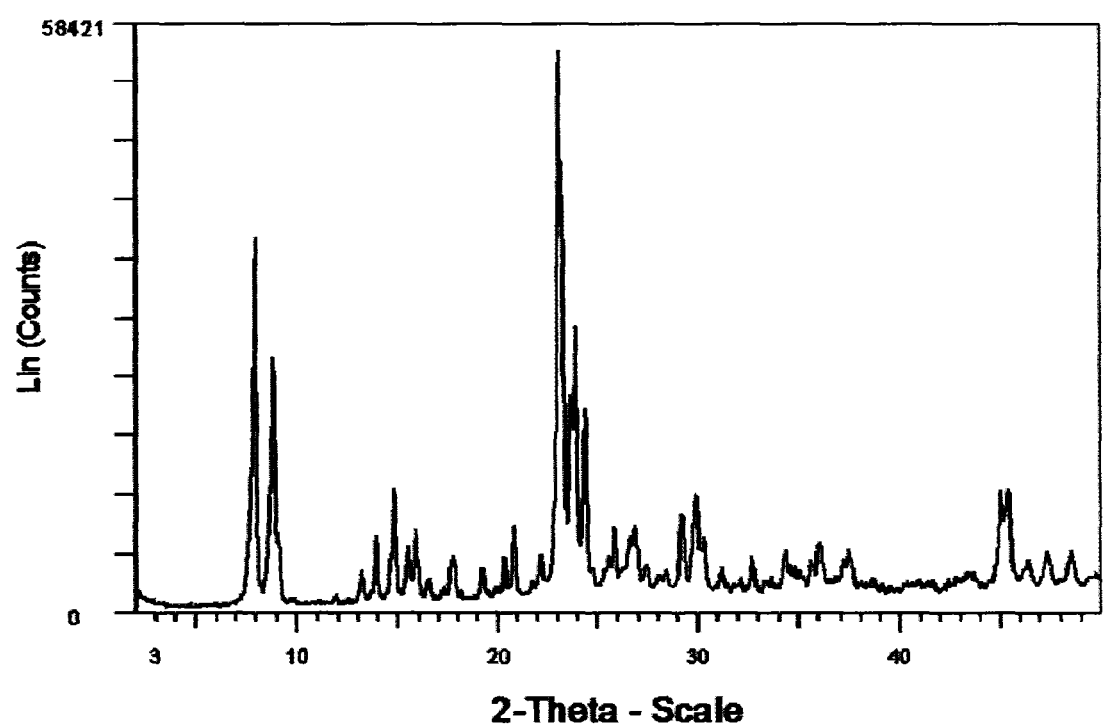
FIG. 5 shows the x-ray diffractogram of the zeolitic material according to example 5. Plotted on the abscissa is the angle (2 theta/°), with explicit values, from left to right, of 3, 10, 20, 30 and 40. Plotted on the ordinate is the signal intensity (Lin (counts)), with explicit values, from bottom to top, of 0 and 58421.
Figure 6:
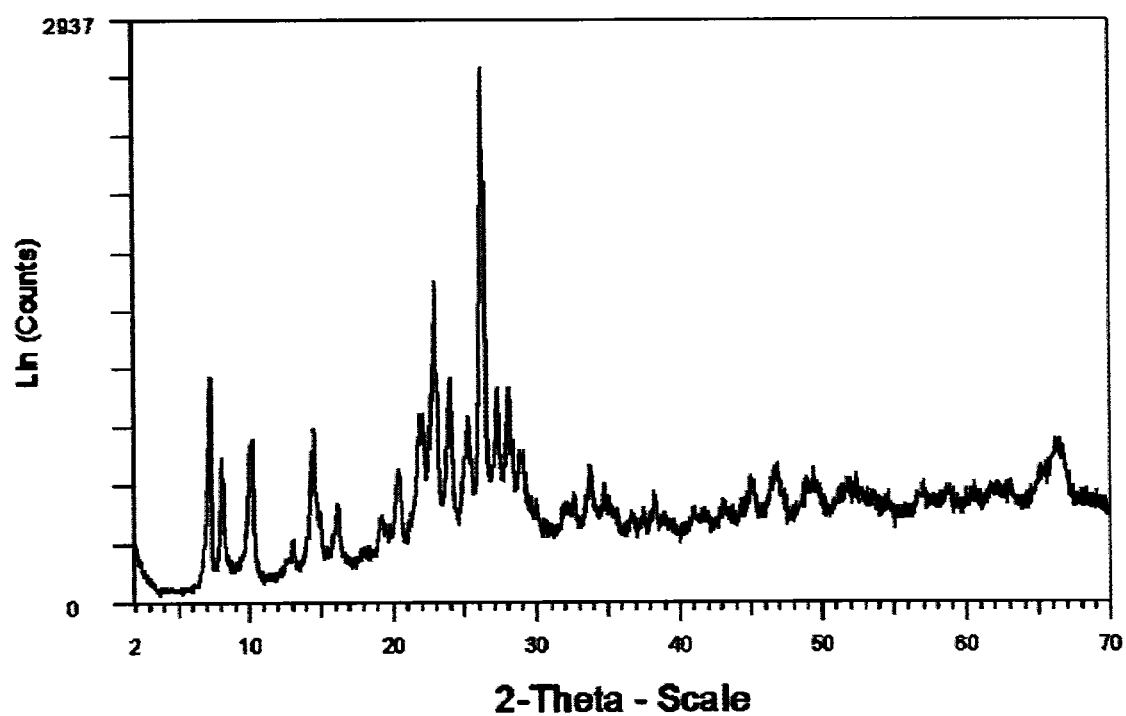
FIG. 6 shows the x-ray diffractogram of the zeolitic material according to example 6. Plotted on the abscissa is the angle (2 theta/°), with explicit values, from left to right, of 2, 10, 20, 30, 40, 50, 60 and 70. Plotted on the ordinate is the signal intensity (Lin (counts)), with explicit values, from bottom to top, of 0 and 2937.
Figure 7:
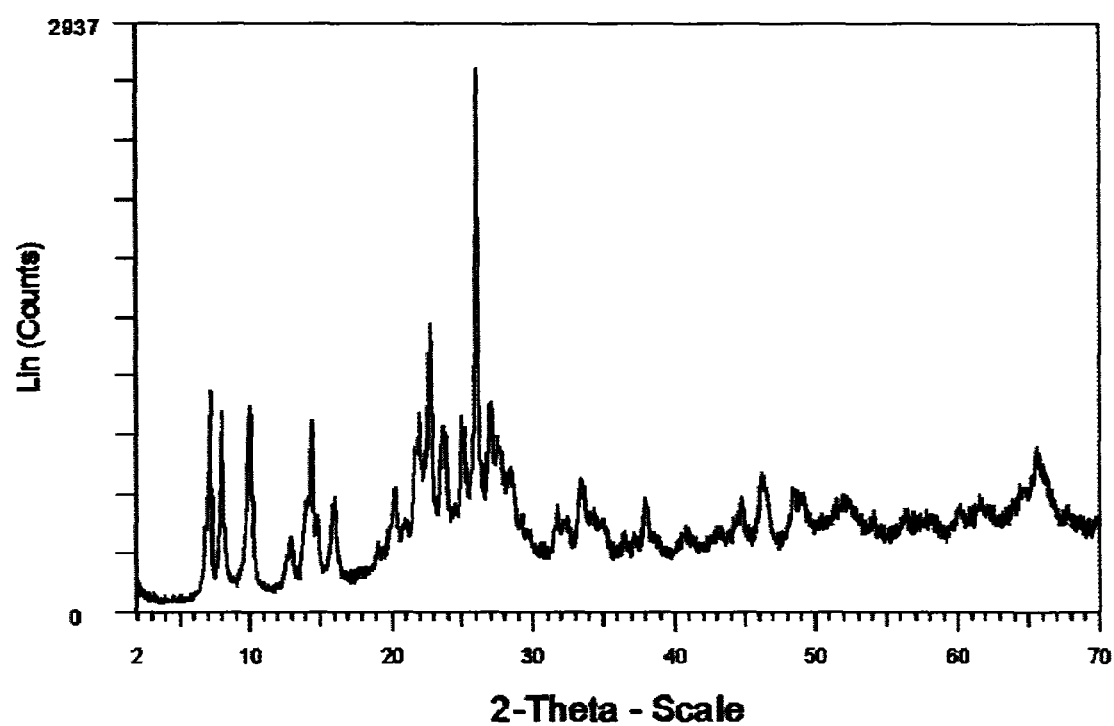
FIG. 7 shows the x-ray diffractogram of the zeolitic material according to example 7. Plotted on the abscissa is the angle (2 theta/°), with explicit values, from left to right, of 2, 10, 20, 30, 40, 50, 60 and 70. Plotted on the ordinate is the signal intensity (Lin (counts)), with explicit values, from bottom to top, of 0 and 2937.
Figure 8:
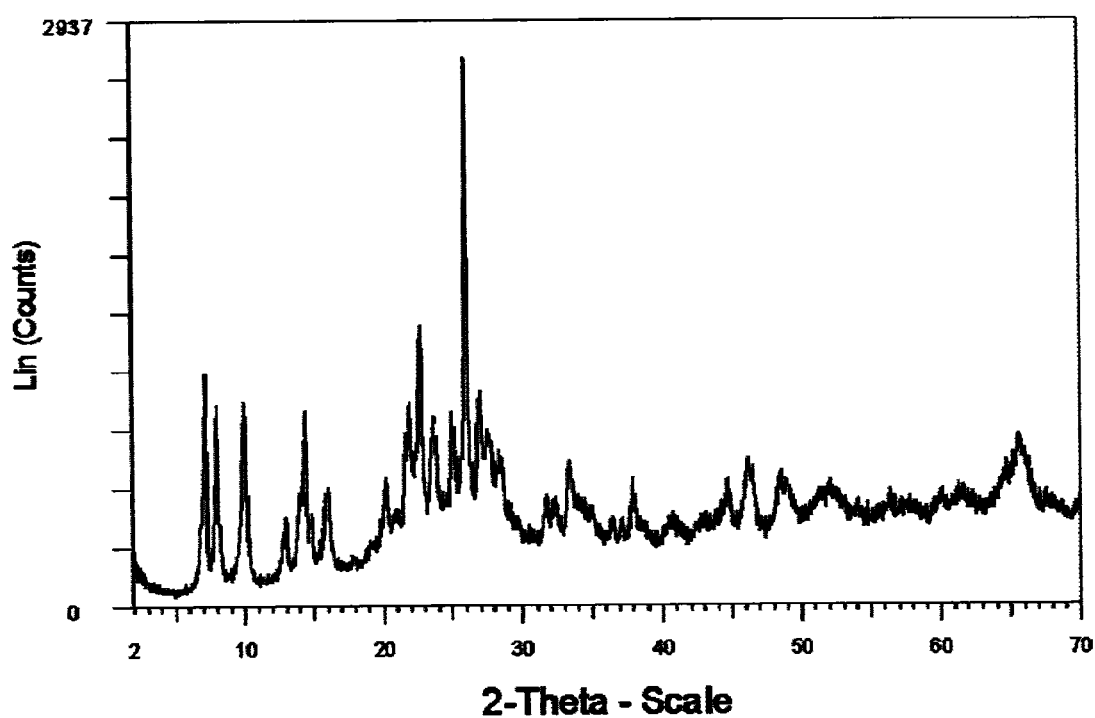
FIG. 8 shows the x-ray diffractogram of the zeolitic material according to example 8. Plotted on the abscissa is the angle (2 theta/°), with explicit values, from left to right, of 2, 10, 20, 30, 40, 50, 60 and 70. Plotted on the ordinate is the signal intensity (Lin (counts)), with explicit values, from bottom to top, of 0 and 2937.
Figure 9:
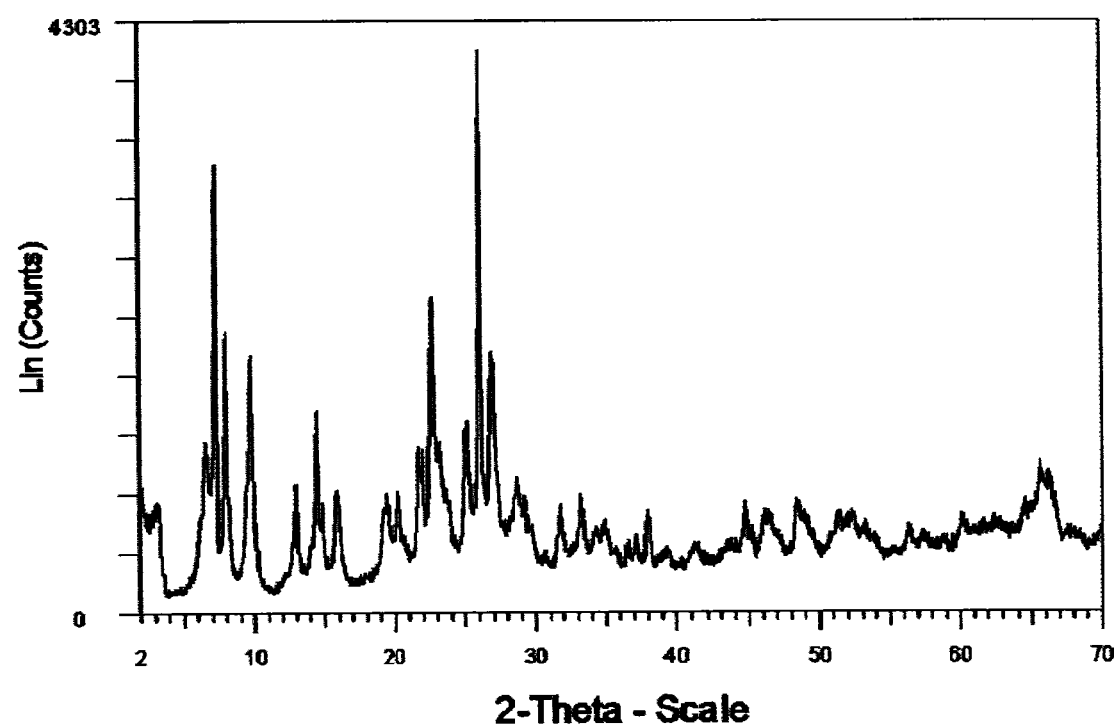
FIG. 9 shows the x-ray diffractogram of the zeolitic material according to example 9. Plotted on the abscissa is the angle (2 theta/°), with explicit values, from left to right, of 2, 10, 20, 30, 40, 50, 60 and 70. Plotted on the ordinate is the signal intensity (Lin (counts)), with explicit values, from bottom to top, of 0 and 4303.

The present invention will now be illustrated further by the examples and comparative examples which follow.

EXAMPLES

I. Analytical Methods
I.1 $NH_3$-TPD
The temperature-programmed desorption of ammonia ($NH_3$-TPD) was conducted in an automated chemisorption analysis unit (Micromeritics AutoChem II 2920) having a thermal conductivity detector. Continuous analysis of the desorbed species was accomplished using an online mass spectrometer (OmniStar QMG200 from Pfeiffer Vacuum). The sample (0.1 g) was introduced into a quartz tube and analyzed using the program described below. The temperature was measured by means of an Ni/Cr/Ni thermocouple immediately above the sample in the quartz tube. For the analyses, He of purity 5.0 was used. Before any measurement, a blank sample was analyzed for calibration.

1. Preparation

Commencement of recording; one measurement per second.

Wait for 10 minutes at 25° C. and an He flow rate of 30 cm$^3$/min (room temperature (about 25° C.) and 1 atm); heat up to 600° C. at a heating rate of 20 K/min; hold for 10 minutes.

Cool down under an He flow (30 cm$^3$/min) to 100° C. at a cooling rate of 20 K/min (furnace ramp temperature);

Cool down under an He flow (30 cm$^3$/min) to 100° C. at a cooling rate of 3 K/min (sample ramp temperature).

2. Saturation with $NH_3$

Commencement of recording; one measurement per second.

Change the gas flow to a mixture of 10% $NH_3$ in He (75 cm$^3$/min; 100° C. and 1 atm) at 100° C.; hold for 30 minutes.

3. Removal of the Excess

Commencement of recording; one measurement per second.

Change the gas flow to an He flow of 75 cm$^3$/min (100° C. and 1 atm) at 100° C.; hold for 60 minutes.

4. $NH_3$-TPD

Commencement of recording; one measurement per second.

Heat up under an He flow (flow rate: 30 cm$^3$/min) to 600° C. at a heating rate of 10 K/min; hold for 30 minutes.

5. End of Measurement

Desorbed ammonia was measured by means of the online mass spectrometer, which demonstrated that the signal from the thermal conductivity detector was caused by desorbed ammonia. This involved utilizing the m/z=16 signal from ammonia in order to monitor the desorption of the ammonia. The amount of ammonia adsorbed (mmol/g of sample) was ascertained by means of the Micromeritics software through integration of the TPD signal with a horizontal baseline.

I.2 Gas Chromatography

The analysis of the gaseous product stream was conducted by means of an online GC-MS system from Agilent. The instrument was equipped with a 10-way valve having two sample loops (500 microliters/1000 microliters) which were operated at 220° C. The detection was effected with the aid of a flame ionization detector (FID) and two thermal conductivity detectors. For the FID flow rate supplied through the front inlet, the following parameters were chosen: injector temperature: 275° C.; split: 1:5. An FFAP column having length 30 m, internal diameter 0.32 mm and film thickness 0.5 micrometer (column flow rate: 5 mL/min) was used. The thermal conductivity detectors were supplied with the sample through the rear inlet in parallel by means of a Y adapter (JAS). Here, the following parameters were chosen: injector temperature: 275° C.; split: 1:2. For the first thermal conductivity detector, a column of the Volamine type having a length of 60 m, an internal diameter of 0.32 mm and a film thickness of 0.45 micrometer (column flow rate: 2 mL/min) was used. The second thermal conductivity detector had a column system with two columns. First column: RTX5 having a length of 30 m, an internal diameter of 0.32 mm and a film thickness of 1 micrometer (column flow rate: 5 mL/min). Second column: "select permanent gases/$CO_2$ HR" having a length of 50 m, an internal diameter of 0.32 mm and a film thickness of 10 micrometers (column flow rate: 2 mL/min). All columns were operated with helium as carrier gas. The GC oven temperature program was as follows:

40° C. (hold time 2.5 min)

heating to 105° C. at a heating rate of 20 K/min (hold time 0 min)

heating to 225° C. at a heating rate of 40 K/min (hold time 2.75 min)

I.3 X-Ray Diffractometry

X-ray diffractograms (Cu K alpha radiation) were recorded on a D8 Advance series 2 diffractometer from Bruker AXS. The diffractometer was equipped with a divergence aperture opening of 0.1° and a Lynxeye detector. On the abscissa is plotted the angle (2 theta), and on the ordinate the signal intensity (Lin (counts)).

I.4 BET Measurements

The specific BET surface areas were determined by means of nitrogen adsorption at 77 K to DIN 66131.

I.5 FTIR Spectroscopy

The IR measurements were effected on a Nicolet 6700 spectrometer. The zeolitic material was compressed to a pellet without the addition of additives. The pellet was introduced into the high-vacuum cell of the IR spectrometer. Before the measurement, the sample was pretreated under high vacuum ($10^{-5}$ mbar) at 300° C. for 3 h. The spectra were recorded after the cell had been cooled down to 50° C. The spectra were recorded within a range from 4000 cm$^{-1}$ to 800 cm$^{-1}$ at a resolution of 2 cm$^{-1}$. The spectra obtained were shown by a plot with the wavenumber on the abscissa and the absorption (in arbitrary units) on the ordinate. For quantitative evaluation of the signal intensities and the ratio of the signals, a baseline correction was undertaken.

I.6 Water Absorption

The isotherms with respect to the water adsorption/desorption were measured on a VTI SA instrument from TA Instruments. The experiment consisted of one pass or a series of passes of a sample which was introduced into the weighing pan of the microbalance within the instrument. Prior to the measurement, the residual moisture was removed from the sample by heating to 100° C. (heating rate 5 K/min) and holding it at this temperature in a nitrogen stream for 6 h. After drying, the temperature in the cell was lowered to 25° C. and kept isothermal during the measurements. The microbalance was calibrated, and the weight of the dried sample served as reference value (maximum deviation in mass: 0.01% by weight). The water absorption of the sample was determined from its increase in weight compared to the dry sample. First of all, an adsorption curve was recorded with increasing relative humidity (RH; in % by weight of water in the atmosphere within the measurement cell) to which the sample was exposed, and the water adsorption of the sample was measured at equilibrium. The relative humidity was increased in steps of 10 percentage points by weight from 5% to 85%. In each step, the system checked the relative humidity, recorded the weight of the sample until attainment of equilibrium conditions, and also recorded the water absorption. The total amount of water that the sample absorbed was determined by exposing the sample to a relative humidity of 85% by weight. During the desorption measurement, the relative humidity was reduced in steps of 10 percentage points from 85% by weight to 5% by weight. The change in weight of the sample (water absorption) was monitored and recorded.

I.7 Particle Size Determination (Dv Values)

1.0 g of the material for which the particle size was to be determined was suspended in 100 g of deionized water and stirred for 1 min. The measurement was conducted by means of a "Mastersizer S long bed version 2.15", serial number 33544-325, from Malvern Instruments GmbH, Herrenberg, Germany.

| | |
|---|---|
| Focal length: | 300 RF mm |
| Beam length: | 10.00 mm |
| Module: | MS 17 |
| Shadowing: | 16.9% |
| Dispersion model: | 3$$D |
| Analysis model: | polydisperse |
| Correction: | none |

I.8 Filtration Resistance

The filtration resistance R(F) of a suspension was determined by the following formula:

$$R(F)=[2*t(end)*A*\text{delta } p]/[V(F,end)*H(end)]$$

where t(end)=end point of the filtration (in s) (defined as the time after the start of the filtration when the liquid level in the filtration apparatus is at the same height as the filtercake)
A=filter area (in m$^2$)
delta p=filtration pressure (in Pa; pressure differential along the filtercake)
V(F,end)=volume of the filtrate at t(end) (in m$^3$)
H(end)=height of the filtercake at t(end) (in m).

The washing resistance R(W) of the filtercake was determined by the following formula:

$$R(W)=[t(end)*A*\text{delta } p]/[V(F,end)*H(end)]$$

where t(end)=end point of the washing (in s) (time after the start of the washing when the liquid level of the washing liquid in the filtration apparatus is at the same height as the filtercake)
A=filter area (in m$^2$)
delta p=filtration pressure (in Pa; pressure differential along the filtercake)
V(F,end)=volume of the filtrate at t(end) (in m$^3$)
H(end)=height of the filtercake at t(end) (in m).

II. Preparation of the Zeolitic Materials

II.1 Example 1: Preparation of a B-Containing Zeolitic Material Having the BEA Structure Type The zeolitic material according to example 1 was prepared according to "Example 6", section 6.1, of WO 2013/117537 A1.

II.2 Example 2: Preparation of an Sn-Containing Zeolitic Material Having the BEA Structure Type First of all, deborated zeolitic material having the BEA structure type was prepared according to "Example 6", sections 6.1 and 6.2, of WO 2013/117537 A1. 50 g of this zeolitic material were introduced into a mixer (Microton MB550 mill) together with 14.2 g of tin(II) acetate (Sn(OAc)$_2$), and the mixture was ground at 14 000 rpm (revolutions per minute) for 15 minutes. After grinding, the mixture was introduced into a porcelain dish and calcined at 500° C. for 3 h under nitrogen, followed by 3 h under air (heating rate 2 K/min). The material obtained had a tin content of 13.1% by weight, a silicon content of 38% by weight and a total organic carbon content (TOC) of less than 0.1% by weight. The specific BET surface area, measured to DIN 66131, was 442 m$^2$/g, the crystallinity, measured by means of x-ray diffractometry, was 44%, and the water absorption was 11.5% by weight. The UV/VIS spectrum showed two maxima, one at a wavelength of 200 nm with a shoulder at 250 nm. In the FT-IR spectrum, the ratio of the intensities between the first absorption band having a maximum between 3701 and 3741 cm$^{-1}$ and a second absorption band having the maximum between 3600 and 3690 cm$^{-1}$ was 1.62. 12 g of the zeolitic material thus obtained were admixed in a round-bottom flask with 360 g of 30% by weight aqueous HNO$_3$ solution, which had a pH in the range from 0 to 1. The mixture was stirred at 100° C. for 20 h (200 rpm). The suspension was filtered and the filtercake was then washed with deionized water at room temperature until the washing water had a pH of about 7. The zeolitic material obtained was dried at 120° C. for 10 h and calcined by heating to 550° C. (2 K/min) and then holding at 550° C. for 5 h. The dried and calcined zeolitic material had a silicon content of 37% by weight, a tin content of 12.6% by weight, a total organic carbon content of less than 0.1% by weight and a crystallinity, determined by means of x-ray diffractometry, of 49%. In addition, the zeolitic material had a specific BET surface area, determined to DIN 66131, of 405 m$^2$/g and the water absorption was 8.7% by weight. The UV/VIS spectrum had a maximum at 210 nm and a shoulder at about 257 nm. In the FT-IR spectrum, the intensity ratio between the first absorption band having a maximum between 3701 and 3741 cm$^{-1}$ and a second absorption band having the maximum between 3600 and 3690 cm$^{-1}$ had the value of 1.5.

II.3 Example 3: Preparation of a B-Containing Zeolitic Material a) 250 kg of demineralized water were initially charged, and 720 kg of hexamethylenediamine were added while stirring at 100 rpm. After stirring for 20 min, the mixture obtained was added to 90 kg of fumed silica (Aerosil 200). After rinsing in with 20 kg of demineralized water, the mixture was homogenized at room temperature with stirring at 70 rpm for 20 h.

b) 80 kg of demineralized water were initially charged. Then 18 kg of boric acid and then 90 kg of hexamethylenediamine were added at 100 rpm while stirring. The mixture was stirred for 4 h.

c) The solution from b) was added to the mixture from a) while stirring at 100 rpm, and it was rinsed in with 10 kg of demineralized water. After stirring for 5 h, a mixture having a pH of 12.6 was obtained.

d) At 100 rpm, the mixture obtained in c) was heated to 165° C. within 3 h and then stirred at 165° C. and stirring at 100 rpm for a further 120 h. Subsequently, the solids were filtered off and the filtercake was dried under N$_2$ for 6 h.

e) An aqueous suspension having a solids content of 30% by weight was produced from the material thus obtained. The suspension was subsequently spray-dried in a spray tower under the following spray-drying conditions:

| | |
|---|---|
| Drying gas, nozzle gas: | technical grade nitrogen |
| Drying gas temperature: | |
| Spray tower temperature (inlet): | 235° C. |
| Spray tower temperature (outlet): | 140° C. |
| Nozzle: | |
| two-component nozzle | supplier: Gerig; size 0 |
| nozzle gas pressure: | 1 bar |
| Working mode: | N$_2$ straight on |
| Instrument used: | spray tower with a nozzle |
| Arrangement: | spray tower - filter - scrubber |
| Gas flow rate: | 1500 kg/h |

-continued

| Filter material: | 20 m² of Nomex ® needlefelt |
| Dosage by means of flexible peristaltic pump: | SP VF 15 (supplier: Verder) | f) The spray-dried material was calcined at 500° C. in a rotary tube with a throughput in the range from 0.8 to 1.0 kg/h. The zeolitic material obtained had a boron content of 0.97% by weight, a silicon content of 44% by weight, a total carbon content (TOC) of <0.1% by weight and a crystallinity of 86%, determined by means of x-ray diffractometry. The specific BET surface area was determined by nitrogen adsorption at 77 K to DIN 66134 to be 380 m²/g. The Langmuir surface area was determined by means of nitrogen adsorption at 77 K to DIN 66131 to be 522 m²/g.

II.4 Example 4: Preparation of an Sn-Containing Zeolitic Material Having the MFI Structure Type A stirred apparatus was initially charged with 575.5 g of TEOS (tetraethyl orthosilicate, Merck), and 14.7 g of Sn[OCH(CH$_3$)$_2$]$_4$*C$_3$H$_7$OH (Alfa Aesar) were added while stirring. Subsequently, 505.9 g of tetrapropylammonium hydroxide and 505.9 g of deionized water were added, and the mixture was stirred for a further 1 h. Thereafter, the alcohol formed was distilled off at 95° C. (bottom temperature) (358 g). Subsequently, the residue was cooled to room temperature. The sol was admixed with 358 g of deionized water; crystallization was effected at 175° C. over 48 h. The sol was diluted 1:1 with water and admixed with aqueous HNO$_3$ solution (5% by weight) until a pH of 7.5 was attained. Subsequently, the solids were filtered off. They were then dried at 110° C. for 24 h and calcined at 550° C. under air for 5 h (heating rate 2 K/min). The yield was 162.9 g.

II.5 Example 5: Preparation of a Ti-Containing Zeolitic Material Having the MFI Structure Type (Titanium Silicalite-1, TS-1)

500 g of tetraethyl orthosilicate and 15 g of tetraethyl titanate were initially charged and admixed with 520 g of a 20.4% by weight aqueous solution of allyltripropylammonium hydroxide (isomer mixture; molar allyl:propenyl ratio 90:10) while stirring. After stirring for one hour, the ethanol formed was distilled off at a bottom temperature of 95° C. The residue obtained was made up to a total court of 1100 g with deionized water. 1000 g of the suspension thus obtained were introduced into an autoclave and treated at internal temperature 175° C. while stirring at 200 rpm for 16 h, in the course of which the pressure increased to 14.5 bar. 100 g were removed from the mixture thus obtained, and the former mixture was spray-dried. 50 g of the spray-dried material were heated under air to 120° C. within 60 min, then the temperature was kept at 120° C. for 240 min. Subsequently, the material was heated to 490° C. within 370 min, then the temperature was kept at 490° C. for 300 min. The zeolitic material obtained had a silicon content of 43.5% by weight, a titanium content of 2.0% by weight and a crystallinity of 99.2%, determined by means of x-ray diffractometry. The specific BET surface area was determined by nitrogen adsorption at 77 K to DIN 66134 to be 436 m²/g. The Langmuir surface area was determined by means of nitrogen adsorption at 77 K to DIN 66131 to be 588 m²/g.

11.6 Example 6: Preparation of an B-Containing Zeolitic Material Having MWW Framework Structure a) Hydrothermal Synthesis 480 kg of deionized water were initially charged in a vessel. While stirring at 70 rpm, 166 kg of boric acid were suspended in this water. The suspension was stirred for a further 3 h. Subsequently, 278 kg of piperidine were added, and the mixture was stirred for a further hour. 400 kg of Ludox® AS-40 were added to the solution obtained, and the solution obtained was stirred at 70 rpm for a further hour. In this synthesis mixture, the boron source boric acid, based on elemental boron, relative to the silicon source Ludox® AS-40, based on elemental silicon, was present in a molar ratio of 1:1; water relative to the silicon source Ludox® AS-40, based on elemental silicon, was present in a molar ratio of 10:1; and the template compound piperidine was present, relative to the silicon source Ludox® AS-40, based on elemental silicon, in a molar ratio of 1.2:1. The mixture thus obtained was transferred to a crystallization vessel and heated to 175° C. under autogenous pressure and while stirring (50 rpm) within 5 h. The temperature of 175° C. was kept essentially constant for 60 h; during these 60 h, the mixture was stirred at 50 rpm. Subsequently, the mixture was cooled to a temperature of 50-60° C. within 5 h. The mother liquor comprising the crystallized B-MWW precursor had a pH of 11.3, as determined with the aid of a pH electrode.

b) pH Adjustment 1400 kg of a 10% by weight aqueous HNO$_3$ solution were added to the mother liquor obtained in a) while stirring at 50 rpm. The addition was effected at a suspension temperature of 40° C. After the addition of the aqueous 10% by weight HNO$_3$ solution, the suspension obtained was stirred further at a suspension temperature of 40° C. at 50 rpm for a further 5 h. The pH of the thus pH-adjusted mother liquor was found to be 7 by means of a pH electrode. The Dv10 value of particles present in the pH-adjusted mother liquor, determined as described in I.7, was 3.0 micrometers, the corresponding Dv50 value was 4.9 micrometers and the corresponding Dv90 value was 8.1 micrometers.

c) Separation

The B-MWW precursor was separated by filtration from the pH-adjusted mother liquor obtained in b), using various filtration devices (suction filter with the filter material Sefar Tetex® Mono 24-1100-SK 012, centrifugal filter, cartridge filter). For all the filter devices, the filtration resistance of the pH-adjusted mother liquor from b) was (30+/−10) mPa*s/m², as described in I.8. The filtercake was then washed with deionized water until the washing water had a conductivity of less than 200 microsiemens/cm. The washing resistance of the filtercake was (30+/−10) mPa*s/m², as described in I.8.

d) Spray-drying and Calcination

An aqueous suspension having a solids content of 15% by weight was produced from the washed filtercake as obtained in c). The suspension was subsequently spray-dried in a spray tower under the following spray-drying conditions:

| Drying gas, nozzle gas: | technical grade nitrogen |
| Drying gas temperature: | |
| Spray tower temperature (inlet): | 270-340° C. |
| Spray tower temperature (outlet): | 150-167° C. |
| Filter temperature (inlet): | 140-160° C. |
| Scrubber temperature (inlet): | 50-60° C. |
| Scrubber temperature (outlet): | 34-36° C. |
| Filter pressure differential: | 8.3-10.3 mbar |
| Nozzle: | |
| two-component nozzle | supplier: Gerig; size 0 |
| nozzle gas temperature: | room temperature |
| nozzle gas pressure: | 2.5 bar |
| Working mode: | N$_2$ straight on |

| | |
|---|---|
| Instrument used: | spray tower with a nozzle |
| Arrangement: | spray tower - filter - scrubber |
| Gas flow rate: | 1900 kg/h |
| Filter material: | 20 m² Nomex ® needlefelt |
| Dosage by means of flexible peristaltic pump: | SP VF 15 (supplier: Verder) |

The spray tower consisted of an upright cylinder having a length of 2650 mm, a diameter of 1200 mm, with conical narrowing of the cylinder at the base. The length of the cone was 600 mm. At the top of the cylinder were disposed the atomizers (a two-component nozzle). The spray-dried material was separated out of the drying gas in a filter downstream of the spray tower, and the drying gas was then conducted through a scrubber. The suspension was conducted through the inner orifice of the nozzle, and the nozzle gas was conducted through an annular gap surrounding the orifice. The spray-dried material was calcined at 650° C. in a rotary tube with a throughput in the range from 0.8 to 1.0 kg/h. The zeolitic material obtained had a boron content of 1.3% by weight, a silicon content of 45% by weight, a total carbon content (TOC) of <0.1% by weight and a crystallinity of 82%, determined by means of x-ray diffractometry. The specific BET surface area was determined by nitrogen adsorption at 77 K to DIN 66134 to be 463 m²/g. The pore volume, determined by means of Hg porosimetry to DIN 66133, was 5.2 m/g. The particle size distribution Dv10 was 5.7 micrometers, Dv50 was 10.56 micrometers and Dv90 was 18.8 micrometers, as described in 1.7.

II.7 Example 7: Preparation of a Ti-Containing Zeolitic Material Having MWW Framework Structure (Ti-MWW)

II.7.1 Preparation of a Deborated Zeolitic Material Having an MWW Framework Structure a) Deboration 1485 kg of water were initially charged in a vessel having a reflux condenser. While stirring at 40 rpm, 99 kg of the spray-dried material obtained according to example 6 were suspended in water. Subsequently, the vessel was closed and the reflux condenser was put into operation. The stirring rate was increased to 70 rpm. While stirring at 70 rpm, the temperature of the contents of the vessel was increased to 100° C. within 10 h and kept at this temperature for 10 h. Then the contents of the vessel were cooled to a temperature less than 50° C. The resulting deborated zeolitic material having an MWW framework structure was separated from the suspension by filtration under a nitrogen pressure of 2.5 bar, and washed four times with deionized water. After filtration, the filtercake was dried in a nitrogen stream for 6 h. The deborated zeolitic material having an MWW framework structure obtained had a residual moisture content of 80%, as determined by means of the IR (infrared) scale at 160° C.

b) Spray-Drying

An aqueous suspension was produced from this nitrogen-dried filtercake with deionized water, and this suspension had a solids content of 15% by weight. This suspension was spray-dried in a spray tower, under the following conditions:

| | |
|---|---|
| Drying gas, nozzle gas: | technical grade nitrogen |
| Drying gas temperature: | |
| Spray tower temperature (inlet): | 290-310° C. |
| Spray tower temperature (outlet): | 140-160° C. |
| Filter temperature (inlet): | 140-160° C. |
| Washer temperature (inlet): | 40-60° C. |
| Washer temperature (outlet): | 20-40° C. |
| Filter pressure differential: | 6.0-10.0 mbar |
| Nozzle: | |
| two-phase nozzle: | manufacturer: Niro; diameter 4 mm |
| nozzle gas pressure: | 2.5 bar |
| Operating mode: | N₂ straight on |
| Equipment used: | spray tower with a nozzle |
| Setup: | spray tower - filter - scrubber |
| Gas flow rate: | 1900 kg/h |
| Filter material: | Nomex ® needlefelt 20 m² |
| Dosage by means of flexible peristaltic pump: | VF 15 (manufacturer: Verder) |

The spray tower comprised a vertical cylinder having a length of 2650 mm and a diameter of 1200 mm, with conical narrowing of the cylinder at the lower end. The length of the cone was 600 mm. A two-phase nozzle was mounted at the top of the cylinder. The spray-dried material was separated from the drying gas in a filter downstream of the spray tower, and the drying gas was then passed through the scrubber. The suspension was passed through the inner orifice of the nozzle, and the nozzle gas was passed through the annular gap that surrounded the orifice.

c) Characterization

The spray-dried zeolitic material obtained with an MWW framework structure had a boron content of 0.08% by weight, a silicon content of 45% by weight and a total organic carbon content (TOC) of <0.1% by weight. The crystallinity was 79%, determined by x-ray diffractometry. The specific BET surface area, determined by nitrogen adsorption at 77 K to DIN 66131, was 451 m²/g, and the pore volume, determined by means of Hg porosimetry to DIN 66133, was 4.99 mL/g. The particle size distribution Dv10 was 5.6 micrometers, Dv50 was 11.1 micrometers and Dv90 was 24.1 micrometers.

II.7.2 Preparation of a Titanium-Containing Zeolitic Material Having an MWW Framework Structure a) Hydrothermal Synthesis Proceeding from the zeolitic material having an MWW framework structure as obtained in II.7.1, a titanium-containing zeolitic material having an MWW framework structure was produced.

| | | |
|---|---|---|
| Starting materials: | deionized water: | 263 kg |
| | piperidine: | 97 kg |
| | tetrabutyl orthotitanate: | 13.8 kg |
| | zeolitic material as obtained in II.7.1: | 64 kg |

64 kg of the zeolitic material having the MWW framework structure were introduced into a tank A. A tank B was initially charged with 150 kg of deionized water and stirred at 80 rpm. 97 kg of piperidine were added while stirring and, during the addition, there was an increase in the temperature of the mixture by about 15° C. Subsequently, 12.8 kg of tetrabutyl orthotitanate and 23 kg of deionized water were added. Subsequently, the mixture was stirred for a further 60 min. The mixture from tank B was then transferred into tank A, and the contents of tank A were stirred at 70 rpm. 90 kg of deionized water were introduced into tank A and then transferred into tank B. After this stirring at 70 rpm, the stirrer speed was reduced to 50 rpm and the mixture from tank B was heated to a temperature of 170° C. within 5 h. At a constant stirring rate of 50 rpm, the temperature of the mixture in tank B was kept essentially under autogenous pressure at a constant temperature of 170° C. for 48 h.

During the crystallization of the titanium-containing zeolitic material having an MWW framework structure, a pressure rise up to 10 bar was observed. Subsequently, the suspension obtained, comprising the titanium-containing zeolitic material having an MWW framework structure, was cooled within 5 h.

b) Spray-drying

The suspension obtained was dissolved in water, in order to attain a water concentration of 85% by weight, and subjected directly to spray drying in a spray tower under the following spray-drying conditions:

| Drying gas, nozzle gas: | technical grade nitrogen |
|---|---|
| Drying gas temperature: | |
| Spray tower temperature (inlet): | 290-310° C. |
| Spray tower temperature (outlet): | 150-170° C. |
| Filter temperature (inlet): | 150-170° C. |
| Scrubber temperature (inlet): | 30-50° C. |
| Scrubber temperature (outlet): | 30-50° C. |
| Filter pressure differential: | 6.0-10.0 mbar |
| Nozzle: | |
| two-phase nozzle: | manufacturer: Niro; diameter 4 mm |
| nozzle gas pressure: | 1.5 bar |
| Operating mode: | $N_2$ straight on |
| Equipment used: | spray tower with a nozzle |
| Setup: | spray tower - filter - scrubber |
| Gas flow rate: | 1800 kg/h |
| Filter material: | Nomex ® needlefelt 20 m² |
| Dosage by means of flexible peristaltic pump: | SP VF 15 (manufacturer: Verder) |

The spray tower consisted of an upright cylinder having a length of 2650 mm, a diameter of 1200 mm, with conical narrowing of the cylinder at the base. The length of the cone was 600 mm. At the top of the cylinder were disposed the atomizers (a two-phase nozzle). The spray-dried material was separated out of the drying gas in a filter downstream of the spray tower, and the drying gas was then conducted through a scrubber. The suspension was conducted through the inner orifice of the nozzle, and the nozzle gas was conducted through an annular gap surrounding the orifice.

c) Characterization

The spray-dried titanium-containing zeolitic material having an MWW framework structure had a silicon content of 36% by weight, a titanium content of 2.4% by weight and a total organic carbon content (TOC) of <11% by weight, a nitrogen content of 2.3% by weight and a crystallinity of 79%, determined by x-ray diffractometry. The particle size distribution was Dv10 5.3 micrometers, Dv50 11.8 micrometers and Dv90 44.0 micrometers.

II.7.3 Acid Treatment of the Titanium-Containing Zeolitic Material Having an MWW Framework Structure The spray-dried titanium-containing zeolitic material having an MWW framework structure as obtained in II.7.2 was subjected to an acid treatment as described hereinafter.

a) Acid Treatment

| Starting materials: | deionized water: | 1233 kg |
|---|---|---|
| | nitric acid (10% by weight aqueous solution): | 287 kg |
| | spray-dried Ti-MWW obtained according to II.7.2: | 76 kg |

1233 kg of deionized water were introduced into a tank. 287 kg of nitric acid were added and 76 kg of the spray-dried titanium-containing zeolitic material having an MWW framework structure were added while stirring at 50 rpm. The mixture obtained was stirred for a further 15 min. Then the stirring rate was increased to 70 rpm. The mixture in the tank was heated to 100° C. and kept under autogenous pressure at this temperature while stirring for 1 h. The mixture thus obtained was then cooled to a temperature less than 50° C. within one hour.

b) Separation

The cooled mixture was filtered and the filtercake was washed six times with deionized water under a nitrogen stream at 2.5 bar.

c) Spray-drying

A suspension was produced from the filtercake obtained in b) with deionized water, and the suspension had a solids content of 85% by weight. This suspension was subjected to a spray-drying operation in a spray tower under the following spray-drying conditions:

| Drying gas, nozzle gas: | technical grade nitrogen |
|---|---|
| Drying gas temperature: | |
| Spray tower temperature (inlet): | 200-330° C. |
| Spray tower temperature (outlet): | 140-165° C. |
| Filter temperature (inlet): | 140-160° C. |
| Scrubber temperature (inlet): | 50-60° C. |
| Scrubber temperature (outlet): | 20-40° C. |
| Filter pressure differential: | 7.0-11.0 mbar |
| Nozzle: | |
| two-phase nozzle: | manufacturer: Niro; diameter 4 mm |
| nozzle gas throughput: | 23 kg/h |
| nozzle gas pressure: | 2.5 bar |
| Operating mode: | $N_2$ straight on |
| Equipment used: | spray tower with a nozzle |
| Setup: | spray tower - filter - scrubber |
| Gas flow rate: | 1900 kg/h |
| Filter material: | Nomex ® needlefelt 20 m² |
| Dosage by means of flexible peristaltic pump: | S VF 15 (manufacturer: Verder) |

The spray tower consisted of an upright cylinder having a length of 2650 mm, a diameter of 1200 mm, with conical narrowing of the cylinder at the base. The length of the cone was 600 mm. At the top of the cylinder were disposed the atomizers (a two-phase nozzle). The spray-dried material was separated out of the drying gas in a filter downstream of the spray tower, and the drying gas was then conducted through a scrubber. The suspension was conducted through the inner orifice of the nozzle, and the nozzle gas was conducted through an annular gap surrounding the orifice.

d) Characterization

The spray-dried acid-treated titanium-containing zeolitic material with an MWW framework structure had a silicon content of 40% by weight, a titanium content of 1.6% by weight and a total organic carbon content (TOC) of 2.0% by weight.

e) Calcination

The spray-dried material was then calcined at 650° C. in a rotary tube with a throughput in the range from 0.8-1.0 kg/h.

f) Characterization

The calcined material had a silicon content of 44% by weight, a titanium content of 1.8% by weight and a total organic carbon content (TOC) of less than 0.1% by weight. The lattice parameter c of the framework structure had a value of 25.2±0.2 angstrom, determined by means of x-ray diffractometry. The UV/VIS spectrum showed a band having a maximum in the range from 200 to 215 nm, and the UV/VIS spectrum did not exhibit any band having a maximum within a range above 250 nm. The Langmuir surface area was determined by means of nitrogen adsorption at 77

K to DIN 66131 to be 634 m²/g, and the specific BET surface area, determined by means of nitrogen adsorption at 77 K to DIN 66131, was 458 m²/g. The crystallization level, determined by means of x-ray diffractometry, was 84%; the average crystallite size was 30.5 nm. The particle size distribution was 4.5 micrometers for Dv10, 8.5 micrometers for Dv50 and 14.6 micrometers for Dv90.

II.8 Example 8: Preparation of a Zn- and Ti-Containing Zeolitic Material Having MWW Framework Structure (ZnTi-MWW)

The zeolitic material according to example 1 was prepared according to "Reference Example 1", sections 1.1 to 1.5, of WO 2013/117536 A1.

II.9 Example 9: Preparation of a Tin-Comprising Zeolitic Material Having an MWW Framework Structure (Sn-MWW)

First of all, zeolitic material was produced according to example 6, and boron-free zeolitic material was produced therefrom according to example 7, steps a and b. 776.25 g of deionized water were initially charged in a glass vessel, and 375 g of piperidine were added while stirring. 1.45 g of tin(II) acetate (Sn(OAc)$_2$) were added to this suspension, and the suspension was stirred for a further 10 minutes. 172.4 g of the zeolitic [ ]-MWW material mentioned immediately above were added to the mixture, which was stirred at room temperature (200 rpm) for 20 min. The suspension obtained was then introduced into an autoclave. The mixture was treated at a temperature of 170° C. while stirring (100 rpm) for 48 h. Subsequently, the autoclave was cooled to room temperature, and the resulting zeolitic material was separated from the suspension by filtration at room temperature. This was followed by washing with deionized water until the washing water had a conductivity of less than 200 microsiemens/cm. After the filtration, the filtercake was dried at a temperature of 120° C. for 16 h. The dried zeolitic material had a silicon content of 40% by weight and a tin content of 0.42% by weight. 173.4 g of the zeolitic material thus obtained were initially charged in a round-bottom flask, and 5202 g of 30% by weight aqueous HNO$_3$ solution having a pH in the range from 0 to 1 were added. The mixture was stirred at a temperature of 100° C. for a period of 20 h (200 rpm). The suspension was filtered and the filtercake was then washed with deionized water at room temperature until the washing water had a pH of about 7. The zeolitic material obtained was dried at 120° C. for 16 h. Then the zeolitic material was calcined by heating it to 550° C. (2 K/min) and keeping it at this temperature for 10 h. The dried and calcined zeolitic material had a silicon content of 47% by weight and a tin content of 0.46% by weight, and also a c parameter, determined by means of x-ray diffractometry, of 26.91 angstrom. The zeolitic material had a specific BET surface area, determined to DIN 66131, of 520 m²/g and a Langmuir surface area, determined to DIN 66131, of 713 m²/g.

II.10 Comparative Examples

In addition, the commercially available zeolitic materials shown in table 1 were used:

TABLE 1

Materials used in the comparative examples, corresponding manufacturers, product name, molar SiO$_2$:Al$_2$O$_3$ ratio and Na$_2$O content in % by weight

| Comparative example | Manufacturer | Product name | Molar SiO$_2$:Al$_2$O$_3$ ratio | Na$_2$O content/% by weight |
|---|---|---|---|---|
| C1 | Zeochem ® | ZEOcat ® PB (Na-Beta) | 20 | 0.6 |
| C2 | Zeochem ® | ZEOcat ® PZ 2/400 (Na-ZSM-5) | 400 | 0.7 |
| C3 | Zeochem ® | ZEOcat ® FM-8 (Na-Mor) | 12 | 6.8 |
| C4 | Zeolyst ® | NH$_4$-MFI 30 (CBV3024E) | 30 | 0.05 |

III. Catalytic Studies

A stream consisting of trioxane (6.3% by volume; Sigma-Aldrich, 1,3,5-trioxane, ≥99%), acetic acid (83.7% by volume; PanReac AppliChem, acetic acid 100% for analysis C, A0820) and argon (10% by volume; 5.0 purity) was heated to 200° C. and hence evaporated (acetic acid:formaldehyde equivalents=4.4:1). The gaseous mixture was then contacted with a pulverulent aldol condensation catalyst according to examples 1 to 9 and comparative examples C1 to C4 at 260 or 290° C. and 1.1 bar (GHSV: 200 h$^{-1}$).

The temperature was measured at the start of the experiment by means of a thermocouple in the isothermal zone of the reactor, i.e. of the catalyst bed, and corresponds to the temperature at which the reactions were conducted. The product stream was subsequently diluted with nitrogen (purity: 5.0) (N$_2$: product stream=22:1), and the composition was determined by gas chromatography.

The data shown below in tables 2 and 3 show the averaged result, with operation of the process according to the invention for 6 h; tables 4 and 5 show the corresponding data for the comparative examples. The analytical data for the zeolitic materials according to examples 1 to 9 are shown in tables 6 to 8.

TABLE 2

Catalytic results of the inventive examples at a temperature of 290° C.

| Zeolitic material according to ex. | Carbon conversion/%[2] | AA yield/ %[3] | AA selectivity/ %[4] | STY/ kg/kg(cat)/h[5] |
|---|---|---|---|---|
| 1 | 9.61 | 8.43 | 87.58 | 0.0792 |
| 2 | 10.84 | 9.56 | 88.09 | 0.0840 |
| 2b[1] | 11.48 | 10.57 | 91.81 | 0.1239 |
| 3 | 6.87 | 6.01 | 87.46 | 0.0640 |
| 3b[1] | 5.96 | 5.31 | 88.91 | 0.0754 |
| 4 | 16.45 | 13.30 | 80.79 | 0.1314 |
| 4b[1] | 15.94 | 13.63 | 85.41 | 0.1794 |
| 5 | 17.34 | 14.18 | 81.62 | 0.1197 |
| 5b[1] | 17.29 | 14.91 | 85.94 | 0.1677 |
| 6 | 7.83 | 5.71 | 73.01 | 0.0519 |
| 6b[1] | 7.61 | 5.55 | 72.96 | 0.0671 |
| 7 | 10.67 | 6.61 | 61.57 | 0.0657 |
| 8 | 9.62 | 8.34 | 86.31 | 0.0858 |
| 9 | 8.57 | 7.13 | 82.69 | 0.0814 |

(1) Zeolitic material was produced as described in II and used directly; samples without addition of "b" were first subjected to an experiment at 260° C. (cf. table 2), regenerated at 350° C. for 24 h (10% by volume of argon, 2% by volume of oxygen, 88% by volume of nitrogen; GHSV: 2000 h$^{-1}$) and then used at 290° C.

(2) The carbon conversion (C) is calculated by the following equation:

$$C = 100 * (NC^P_{sum} / (NC^E_{FA} + NC^E_{ES}))$$

$NC^P_{sum} = (NC^E_{FA} + NC^E_{ES}) - (NC^P_{FA} + NC^P_{ES})$;
$NC^E_{FA}$ = number of carbon atoms present in stream S4 in the form of a formaldehyde source;
$NC^E_{ES}$ = number of carbon atoms present in stream S4 in the form of acetic acid;
$NG^P_{FA}$ = number of carbon atoms present in product stream S6 in the form of a formaldehyde source;
$NC^P_{ES}$ = number of carbon atoms present in product stream S6 in the form of acetic acid.

(3) The yield (Y) of acrylic acid is calculated by the following formula:

$$Y = 100 * (NC^P_{AS} / (NC^E_{FA} + NC^E_{ES}))$$

$NC^P_{AS}$ = number of carbon atoms present in product stream S6 in the form of acrylic acid.

(4) The acrylic acid selectivity (S) is calculated by the following formula:

$$S = 100 (NC^P_{AS} / NC^P_{sum}).$$

(5) The space-time yield (STY) represents the ratio of the mass flow rate of acrylic acid in stream S6 in [mass/time] to the mass of the aldol condensation catalyst in (ii) in [mass]; unit: [kg acrylic acid/kg aldol condensation catalyst/h]

TABLE 3

Catalytic results of the inventive examples at a temperature of 260° C.

| Zeolitic material according to ex. | Carbon conversion/% | AA yield/% | AA selectivity/% | STY/ kg/kg(cat)/h |
|---|---|---|---|---|
| 1 | 7.20 | 6.39 | 88.73 | 0.060 |
| 2 | 8.78 | 8.13 | 92.64 | 0.071 |
| 3 | 4.14 | 3.51 | 84.70 | 0.037 |
| 4 | 11.08 | 8.74 | 80.38 | 0.086 |
| 5 | 14.77 | 11.19 | 75.72 | 0.094 |
| 6 | 4.92 | 2.99 | 60.77 | 0.027 |
| 7 | 10.24 | 6.48 | 63.09 | 0.064 |
| 8 | 8.13 | 7.54 | 92.67 | 0.078 |
| 9 | 7.45 | 6.77 | 90.76 | 0.077 |

TABLE 4

Catalytic results of the comparative examples at a temperature of 290° C.

| Ex. | Carbon conversion/% | AA yield/% | AA selectivity/% | STY/ kg/kg(cat)/h |
|---|---|---|---|---|
| C1 | 5.01 | 3.22 | 64.24 | 0.0347 |
| C2 | 5.10 | 4.65 | 91.10 | 0.0407 |
| C3 | 3.20 | 0.77 | 24.10 | 0.0063 |
| C4 | 7.18 | 5.26 | 77.39 | 0.0583 |

TABLE 5

Catalytic results of the comparative examples at a temperature of 260° C.

| Ex. | Carbon conversion/% | AA yield/% | AA selectivity/% | STY/ kg/kg(cat)/h |
|---|---|---|---|---|
| C1 | 5.74 | 5.29 | 92.26 | 0.057 |
| C2 | 1.51 | 1.19 | 79.28 | 0.010 |
| C3 | 6.20 | 0.45 | 7.84 | 0.004 |
| C4 | 10.28 | 8.74 | 86.60 | 0.072 |

TABLE 6

Analysis of examples 1 to 5, 7 and 8 with regard to NH$_3$-TPD and IR spectroscopy

| Zeolitic material according to ex. | NH$_3$-TPD/mmol NH$_3$/g cat. | | | FTIR[6] | | |
|---|---|---|---|---|---|---|
| | 0 to 250° C. | 251 to 500° C. | 501 to 700° C. | 3790 to 3691 cm$^{-1}$ | 3690 to 3591 cm$^{-1}$ | 3590 to 3490 cm$^{-1}$ |
| 1 | 0.3 | | | X | | |
| 2 | 0.088 | 0.015 | 0.009 | X | | X |
| 3 | 0.366 | | | X | X | |
| 4 | 0.25 | | 0.015 | X | X | X |
| 5 | 0.05 | | | X | X | X |
| 7 | 0.0600 | | | X | X | X |
| 8 | 0.19 | 0.076 | | X | X | X |

[6]Marking with "X" means that the particular IR spectrum had at least one maximum in an absorption band within the range specified.

TABLE 7

Analysis of examples 1 to 5 and 7 to 9 with regard to X and Y content (reported in brackets; determined by means of elemental analysis), specific BET surface area; water absorption

| Zeolitic material according to ex. | X and/or Y content/ % by weight | BET/ m$^2$/g | Water absorption/% |
|---|---|---|---|
| 1 | 1.35 (B) | 498 | 18.9 |
| 2 | 12.8 (Sn) | 393 | 7.00 |
| 3 | 0.97 (B) | 380 | 11.9 |
| 4 | 1.7 (Sn) | | 4.34 |
| 5 | 2 (Ti) | 454 | 8.46 |
| 7 | 1.8 (Ti) | 459 | |
| 8 | 1.8 (Ti) | 441 | 9.2 |
| | 1.3 (Zn) | | |
| 9 | 0.46 (Sn) | 520 | |

TABLE 8

Analysis of examples 1 to 9 with regard to Al, Na, K, Mg and Ca content

| Zeolitic material according to ex. | Content (in % by weight) | | | | |
|---|---|---|---|---|---|
| | Al | Na | K | Mg | Ca |
| 1 | 0.02 | 0.011 | <0.01 | <0.01 | <0.01 |
| 2 | 0.005 | <0.01 | <0.01 | <0.01 | <0.01 |
| 3 | <0.01 | <0.01 | <0.01 | <0.01 | <0.01 |
| 4 | <0.01 | 0.06 | <0.01 | <0.01 | <0.01 |
| 5 | <0.01 | 0.01 | <0.01 | <0.01 | <0.01 |
| 6 | 0.02 | <0.01 | <0.01 | <0.01 | 0.02 |
| 7 | 0.04 | <0.03 | <0.01 | <0.01 | <0.01 |
| 8 | 0.03 | <0.01 | <0.01 | <0.01 | <0.01 |
| 9 | 0.02 | <0.01 | <0.01 | <0.01 | <0.01 |

The values reported in table 8 were determined, after digestion, by means of atomic absorption spectroscopy AAS (Na, K) or by means of atomic emission spectrometry ICP/OES (Al, Ca, Mg).

As can be inferred from the results, all the inventive examples, at a temperature of 290° C., show higher space-time yields and yields of acrylic acid than comparative examples C1 to C4. In addition, inventive examples 1 and 2, and also 4 to 9, show higher carbon conversions. At a temperature of 260° C., inventive examples 4, 5, 8 and 9 show higher space-time yields than all the comparative examples C1 to C4. Moreover, for example, inventive examples 4 and 5 have better carbon conversions than all the comparative examples. Therefore, the invention provides a process for preparing acrylic acid using a formaldehyde source and acetic acid as reactants, which, through the use of a zeolitic material, zeolitic material not comprising any aluminum, gives better catalytic results, particularly with regard to carbon conversion, yield of acrylic acid and selectivity of acrylic acid formation, and especially with regard to space-time yield.

U.S. Provisional Patent Application No. 62/004,961, filed 30 May 2014, is incorporated into the present application by literature reference. With regard to the abovementioned teachings, numerous changes and deviations from the present invention are possible. It can therefore be assumed that the invention, within the scope of the appended claims, can be performed differently from the way described specifically herein.

LITERATURE CITED

Vitcha and Sims, I & EC Product Research and Development, Vol. 5, No. 1, March 1966, pages 50 to 53
Wierzchowsky and Zatorski, Catalysis Letters 9 (1991), pages 411 to 414
DE 2010 040 921 A1
DE 2010 040 923 A1
US 2013/0085294 A1

The invention claimed is:

1. A process for preparing acrylic acid, the process comprising
contacting a stream S4 comprising a formaldehyde source and acetic acid with an aldol condensation catalyst comprising a zeolitic material to obtain a stream S6 comprising acrylic acid;
wherein
a framework structure of the zeolitic material comprises Si, O, and optionally Al, and one or more elements selected from the group consisting of a tetravalent element Y other than Si and a trivalent element X other than Al; and
the framework structure of the zeolitic material has a molar Al:Si ratio of from 0:1 to 0.001:1.

2. The process according to claim 1, wherein the framework structure of the zeolitic material comprises $YO_2$ where Y is optionally selected from the group consisting of Sn, Ti, Zr, Ge, V and any combination thereof.

3. The process according to claim 1, wherein the framework structure of the zeolitic material comprises $X_2O_3$ where X is optionally selected from the group consisting of B, In, Ga, Fe, Ta and any combination thereof.

4. The process according to claim 1, wherein zeolitic material comprises one or more non-framework elements Z selected from the group consisting of Ti, Zr, V, Nb, Ta, Cr, Mo, W, Mn, Fe, Co, Ni, Zn, Ga, Ge, In, Sn, Pb, P, N and S.

5. The process according to claim 1, wherein the zeolitic material has a structure selected from the group consisting of BEA, MFI, MWW, FAU, MOR, CHA, LEV, FER, MEL, MOR, AFI, RRO, CDO and any combination thereof.

6. The process according to claim 1, wherein the zeolitic material has a structure of BEA and optionally has a molar (Si+Y):X ratio of from 2:1 to 500:1.

7. The process according to claim 1, wherein the zeolitic material has a structure of MEI, MEL, or any combination thereof and optionally has a molar (Si+Y):X ratio of from 2:1 to 500:1.

8. The process according to claim 1, wherein the zeolitic material has a structure of MWW, optionally has a molar (Si+Y):X ratio of from 2:1 to 500:1, and optionally comprises Zn as a non-framework element.

9. The process according to claim 1, wherein a total content of alkali metal and alkaline earth metal in the zeolitic material, calculated as alkali metal oxide ($M_2O$) and alkaline earth metal oxide (MO), is from 0% to 0.1% by weight, based on a total weight of the zeolitic material.

10. The process according to claim 1, wherein the aldol condensation catalyst further comprises a binder material which is optionally selected from the group consisting of graphite, $SiO_2$, $TiO_2$, $ZrO_2$, MgO, any combination thereof and a mixed oxide of at least two elements selected from the group consisting of Si, Ti, Zr, Mg and any combination thereof.

11. The process according to claim 1, wherein the aldol condensation catalyst is in a form of shaped bodies, in a star shape, in a tablet form, in a form of spheres, or in a form of hollow cylinders.

12. The process according to claim 1, wherein a molar ratio of acetic acid to formaldehyde, obtained and/or obtainable from the formaldehyde source, in the stream S4 ranges from 0.01:1 to 10:1, and the stream S4 optionally further comprises one or more diluents which optionally are selected from the group consisting of nitrogen, carbon monoxide, carbon dioxide, ethene, acetone, water, and any combination thereof.

13. The process according to claim 1, wherein
the contacting is effected at a temperature of from 200 to 400° C.,
the stream S4 prior to the contacting is optionally brought to a temperature of from 150 to 250° C., the contacting is effected at a pressure of from 0.01 to 10 bar, and
the contacting is effected at a space velocity (GHSV) of from 50 to 10 000 $h^{-1}$.

14. The process according to claim 1, wherein a space-time yield of the contacting ranges from 0.01 to 2.5 kg/kg/h, and the space-time yield is defined as kg(acrylic acid)/kg (aldol condensation cataltyst)/h.

15. The process according to claim 1, further comprising regenerating the aldol condensation catalyst optionally at a temperature of from 300 to 700° C. and optionally in the presence of oxygen.

16. The process according to claim 1, wherein the formaldehyde source is an anhydrous formaldehyde source.

17. The process according to claim 1, wherein
a temperature-programmed desorption with $NH_3$ (NH3TPD) of the zeolitic material has a desorption spectrum with a desorption maximum within at least one of temperature ranges of from 0 to 250° C., from 251 to 500° C., and from 501 to 700° C., and
following deconvolution of the desorption spectrum, the desorption maximum in the temperature range of 0 to 250° C. has a concentration of desorbed $NH_3$ of from 0.001 to 1.0 mmol/g, the desorption maximum in the temperature range of 251 to 500° C. has a concentration of desorbed $NH_3$ of from 0.001 to 0.5 mmol/g, and the desorption maximum in the temperature range 501 to 700° C. has a concentration of desorbed $NH_3$ of from 0.001 to 0.1 mmol/g, where the concentration of desorbed $NH_3$ is defined as mmol(desorbed $NH_3$)/g(zeolitic material).

18. The process according to claim 1, wherein the aldol condensation catalyst further comprises from 0% to 1% by weight of vanadium, calculated as vanadium oxide and based on a total weight of the aldol condensation catalyst.

* * * * *